US012213992B2

(12) United States Patent
Hider et al.

(10) Patent No.: US 12,213,992 B2
(45) Date of Patent: Feb. 4, 2025

(54) IRON CONTAINING COMPOSITION AND USE THEREOF

(71) Applicant: RENAPHARMA AB, Stockholm (SE)

(72) Inventors: Robert Hider, Essex (GB); Peter Geisser

(73) Assignee: RENAPHARMA AB, Stockholm (SE)

( * ) Notice: Subject to any disclaimer, the term of this patent is extended or adjusted under 35 U.S.C. 154(b) by 791 days.

(21) Appl. No.: 17/272,756

(22) PCT Filed: Sep. 5, 2019

(86) PCT No.: PCT/EP2019/073637
§ 371 (c)(1),
(2) Date: Mar. 2, 2021

(87) PCT Pub. No.: WO2020/049074
PCT Pub. Date: Mar. 12, 2020

(65) Prior Publication Data
US 2021/0205356 A1 Jul. 8, 2021

(30) Foreign Application Priority Data
Sep. 5, 2018 (EP) ..................................... 18192831

(51) Int. Cl.
| | | |
|---|---|---|
| A61K 33/26 | (2006.01) | |
| A23D 7/005 | (2006.01) | |
| A23L 33/12 | (2016.01) | |
| A23L 33/165 | (2016.01) | |
| A61K 9/10 | (2006.01) | |
| A61K 31/23 | (2006.01) | |
| A61P 7/06 | (2006.01) | |

(52) U.S. Cl.
CPC ............ *A61K 33/26* (2013.01); *A23D 7/0053* (2013.01); *A23L 33/12* (2016.08); *A23L 33/165* (2016.08); *A61K 9/10* (2013.01); *A61K 31/23* (2013.01); *A61P 7/06* (2018.01)

(58) Field of Classification Search
None
See application file for complete search history.

(56) References Cited

U.S. PATENT DOCUMENTS

| | | |
|---|---|---|
| 2,938,027 A | 5/1960 | Gladstone |
| 4,454,113 A | 6/1984 | Hemker |
| 5,330,759 A | 7/1994 | Pagay et al. |
| 5,434,277 A | 7/1995 | Hwu et al. |
| 7,705,169 B2 | 4/2010 | Duceppe et al. |
| 9,241,876 B2 | 1/2016 | Zheng et al. |
| 9,775,814 B2 | 10/2017 | Teles et al. |
| 2018/0014557 A1 | 1/2018 | Wan et al. |

FOREIGN PATENT DOCUMENTS

| | | | |
|---|---|---|---|
| CN | 102 630 760 | 8/2012 | |
| CN | 107 343 657 | 11/2017 | |
| EP | 2241314 B1 | 4/2013 | |
| EP | 2571379 B1 | 7/2014 | |
| WO | 2005041928 A1 | 5/2005 | |
| WO | 2008016743 | 2/2008 | |
| WO | WO-2008016743 A2 * | 2/2008 | ............. A23L 29/10 |
| WO | 2012033812 | 3/2012 | |
| WO | 2012094598 A2 | 7/2012 | |
| WO | 2014140991 | 9/2014 | |
| WO | 2016126234 A1 | 8/2016 | |
| WO | 2017075215 | 5/2017 | |
| WO | 2018007476 A1 | 1/2018 | |

OTHER PUBLICATIONS

Abrahamson, H.B., et al., "Synthesis and characterization of iron stearate compounds", J. Inorganic Biochemistry, 54(2) Jan. 1, 1994 (Year: 1994).*
Abrahamson H B et al., "Synthesis and characterization of iron stearate compounds" Journal of Inorganic Biochemistry, Elsevier Inc., US, vol. 54, No. 2, pp. 115-130 Jan. 1, 1994.
Database WPI, Week 201780 Thomson Scientific, London GB; An 2017-78657P XP002788838.
Database WPI, Week 201281 Thomson Scientific, London GB; An 2012-P96557 XP002788839.
Amara et al., "In vitro digestion of citric acid esters of mono- and diglycerides (CITREM) and CITREM-containing infant formula/emulsions" Food Funct., 2014, 5, 140-9.

* cited by examiner

*Primary Examiner* — H. Sarah Park
(74) *Attorney, Agent, or Firm* — Renner, Otto, Boisselle & Sklar, LLP

(57) ABSTRACT

A composition comprising an iron salt of a C8 to C24 fatty acid, a citric acid ester of mono- and/or diglyceride or a mixture of citric acid esters of mono- and/or diglyceride and optionally a fatty acid or a mixture of fatty acids, and a method for preparing such a composition. The composition is useful as a medicament for the treatment and prophylaxis of iron deficiency, as a dietary supplement, and as a food additive.

15 Claims, 12 Drawing Sheets

IRON CONTAINING COMPOSITION AND USE THEREOF

This application is a national phase of International Application No. PCT/EP2019/073637 filed Sep. 5, 2019 and published in the English language, which claims priority to European Application No. 18192831.8 filed Sep. 5, 2018, both of which are hereby incorporated herein by reference.

FIELD OF THE INVENTION

The present invention relates to iron containing compositions and use thereof, e.g. in therapy, in particular in the treatment or prophylaxis of iron deficiency and iron deficiency anaemia. More particularly, the invention relates to an iron containing composition suitable for oral use in the treatment or prevention of iron deficiency.

BACKGROUND OF THE INVENTION

Iron (Fe) is an element present in all cells in the body of an animal, with several vital functions, such as transport of oxygen, electron transport, and synthesis of DNA.

Physiologically, iron is lost from the body by excretion via mainly feces and urine, as well by e.g. loss of blood, such as in menstruating fertile women. An inadequate intake of iron to compensate for the loss of iron from the body will result in development of iron deficiency, which if uncorrected will lead first to so-called latent iron deficiency (LID), followed by iron-deficient erythropoiesis (IDE), and finally iron deficiency anaemia.

In addition to physiological losses of iron, various pathologic conditions are associated with iron deficiency and iron deficiency anaemia due to either excessive losses of blood and/or difficulties in absorbing iron. The cause of gastrointestinal losses may be gastrointestinal bleeding in diseases such as inflammatory bowel disease, malignancy or gastric ulcers. Malabsorption of iron may occur due to difficulties in absorbing iron which may occur in celiac disease, Crohn's disease or after gastric surgery.

Some symptoms of iron deficiency anaemia are general weakness, dizziness, extreme fatigue, fast heartbeat, paler than normal skin, chest pain, headaches etc. If the anaemia is left untreated, additional complications may occur related to the heart such as heart failure and subsequent enlargement of the heart for compensating the lack of oxygen. In children and infants, iron deficiency may cause growth retardation and irreversible cognitive disturbances.

Iron deficiency during pregnancy increases the risk of pregnancy complications, including an increased risk for premature birth and placenta insufficiency. The fetus of a pregnant woman with iron deficiency has an increased risk of intrauterine death as well as an increased risk of schizophrenia later on in life.

Population groups more frequently subjected to iron deficiency than others include fertile and pregnant women, anorectics, elderly, vegetarians, and blood donors. Furthermore, iron deficiency is common in connection with various disorders and conditions, such as inflammatory bowel disease, cancer, e.g. cancer of the gastrointestinal system, chronic kidney disease, heavy uterine bleeding, and post partum. In many developing countries, iron deficiency also may follow from various parasitic infections, e.g. malaria or worm infections.

Treatment of iron deficiency, including iron deficiency anaemia, normally involves increasing the iron intake, often by use of iron containing medication, either by parenteral or enteral, e.g. oral administration. The most common form of iron preparations are oral preparations, in either liquid or solid form (e.g. tablets and capsules). The most common iron medications are tablets for oral administration, e.g. containing an iron salt such as iron sulfate. However, many oral iron medications are limited by side effects such as nausea, constipation, or diarrhea, which may result in low patient compliance. Additionally, the iron uptake is often very low; often less than 10% and sometimes as little as 1% of the administered iron is absorbed, which may result in an unacceptably slow rate of increase of the iron level in the blood, in particular in situations where a rapid increase is desirable, such as in cases of severe anaemia. A low rate of absorption is particularly common in the presence of inflammation which causes the iron regulatory protein hepcidin to inhibit the uptake of iron in the gut.

In case of slow response and/or poor tolerability, iron may have to be administered parenterally, e.g. by intravenous injection or infusion. Such administration, though often efficient to combat iron deficiency, is hampered by being more expensive, requiring medical staff to administer the iron, and by the experienced discomfort typically linked with the mode of administration. It also requires the patient to visit a hospital unit to receive treatment which may be time consuming and cause absence from work.

Consequently, there still is a medical need for further iron containing preparations, preferably with reduced side effects and high uptake in the body independently of the presence of inflammation, and that may preferably be orally administered.

SUMMARY OF THE INVENTION

A first aspect is a composition comprising (i) a Fe salt of a C8 to C24 fatty acid salt; and (ii) a citric acid ester of mono- and/or diglyceride or a mixture of citric acid esters of mono- and/or diglyceride.

In some embodiments, a composition is provided comprising (i) a Fe salt of a C8 to C24 fatty acid salt; (ii) a citric acid ester of mono- and/or diglyceride or a mixture of citric acid esters of mono- and/or diglyceride; and (iii) a C8 to C24 fatty acid or a salt thereof.

A further aspect is a composition as disclosed herein, for use in therapy, e.g. in the treatment of iron deficiency or a disorder associated with iron deficiency.

A further aspect is a composition as disclosed herein, for use in the prophylaxis of iron deficiency or a disorder associated with iron deficiency.

A further aspect is a pharmaceutical formulation comprising a therapeutically effective amount of a composition as disclosed herein, and optionally a pharmaceutically acceptable excipient.

A further aspect is the use of a composition as disclosed herein as a food additive, or in the preparation of a food additive, or in the preparation of a foodstuff.

A further aspect is a food additive or foodstuff comprising the composition as disclosed herein.

A further aspect is a method for the preparation of an iron containing composition, by admixing an iron salt, e.g. a Fe(III) salt, a citric acid ester of mono- and/or diglyceride or mixture of citric acid esters of mono- and/or diglyceride, and optionally one or more fatty acids; adding water and a basifying agent; and processing the mixture to obtain a stable dispersion.

Also provided herein is a method for the treatment of iron deficiency or a disease or disorder associated with or caused by iron deficiency, by administration of a therapeutically effective amount of a composition or formulation as disclosed herein to a warm-blooded animal, e.g. a mammal, in particular a human, in need of such treatment.

Further provided herein is the use of a composition as disclosed herein in the manufacturing of a medicament for the treatment of iron deficiency or a disease or disorder associated with or caused by iron deficiency.

DETAILED DESCRIPTION OF THE INVENTION

Definitions

Figure 1:
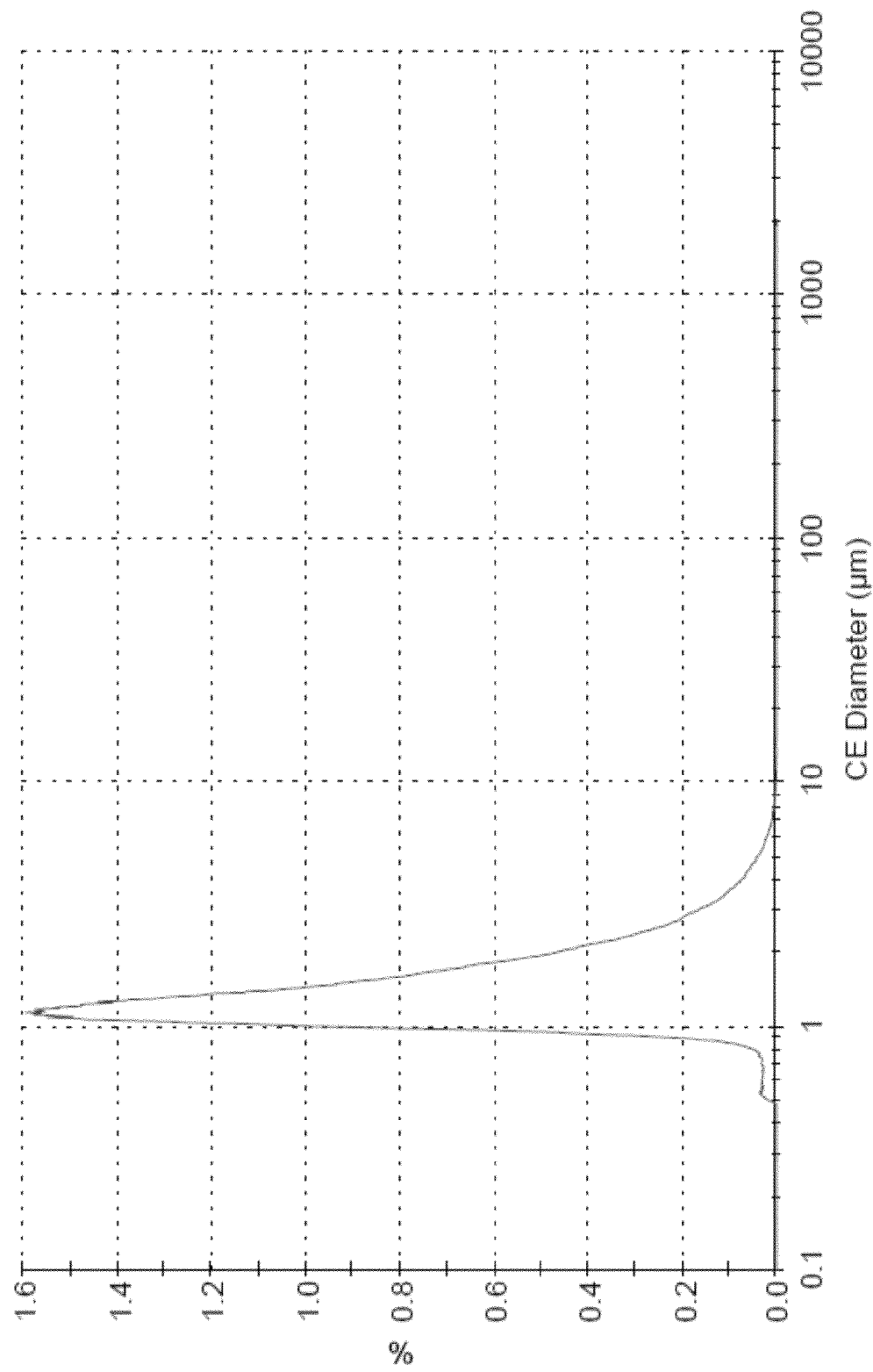
FIG. 1 is a size distribution curve of particles in the dispersion of Example 1, obtained using bright field microscopy.

As used herein, the indefinite articles "a" and "an" and the definite article "the" include plural as well as single referents, unless the context clearly indicates otherwise.

As used herein, "administration", "administering" etc. means the giving of, dispensing of, or application of medicines, drugs, or remedies to a subject (e.g. a mammal, preferably a human).

As used herein, "effective" refers to an amount (e.g. of the inventive composition) that is sufficient to yield a desired therapeutic response without undue adverse side effects (such as toxicity, irritation, or allergic response), commensurate with a reasonable benefit/risk ratio when used in therapy.

As used herein, "pharmaceutically acceptable" refers to that which is suitable for use with humans and/or animals, generally safe and non-toxic at normal use, i.e. without undue adverse side effects (such as toxicity, irritation, and allergic response) commensurate with a reasonable benefit/risk ratio.

As used herein, "excipient" is a substance formulated alongside the active ingredient of a medication included for such purposes as long-term stabilization, to provide bulk to a solid formulation, to act as a carrier and/or diluent, to confer a therapeutic enhancement on the active ingredient in the final dosage form, e.g. by facilitating absorption, reducing viscosity, or enhancing solubility. An excipient can also be useful in the manufacturing process, e.g. by facilitating powder flowability or providing non-stick properties. Examples of excipients are antiadherents, binders, coatings, colours, disintegrants, flavours, glidants, lubricants, preservatives, sorbents, sweeteners, and vehicles (carriers).

As used herein, a "symptom" includes any clinical or laboratory manifestation associated with a disorder or disease and is not limited to what a subject can feel or observe.

As used herein, "treating", "treatment" etc. includes preventing a condition, disorder or disease from occurring and/or ameliorating, reversing or curing a condition, disorder or disease, in a treated subject, e.g. a mammal, preferably a human.

As used herein a "subject" or "patient" refers to a worm-blooded animal (including humans) selected from mammals and birds.

A "mammal" preferably refers to a human, but also includes non-human animals, such as pet animals (e.g. dogs and cats), farm animals (e.g. cow, pig and sheep), horses etc.

A "bird" refers to any type of bird, e.g. a poultry, such as a hen, a chicken, a turkey, a goose, or a cage bird, such as a parakeet, a parrot etc.

As used herein, the term "sustained release" refers to the release of active ingredient from an oral dosage form at such a rate that blood (e.g., plasma) concentrations (levels) are maintained within the therapeutic range but below toxic levels over an extended period of time, e.g. for up to 24 hours or even more.

As used herein, the term "delayed release" refers to the release of active ingredient from an oral dosage form which does not occur immediately on ingestion by a subject, but is delayed until the dosage reaches a target site in the body of the subject, e.g. the intestine.

As used herein "monoglyceride" (or "monoacylglycerol") refers to a compound of formula

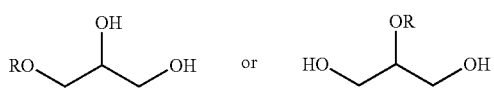

wherein R is an acyl group R'—C(O)—, and R' is a saturated or unsaturated aliphatic group.

As used herein "saturated mono- or diglyceride" refers to a mono- or diglyceride as defined herein above wherein each R' is a saturated aliphatic moiety.

As used herein "unsaturated mono- or diglyceride" refers to a mono- or diglyceride as defined herein above wherein at least one R' is an unsaturated aliphatic moiety.

As used herein "diglyceride" (or "diacylglycerol") refers to a compound of formula

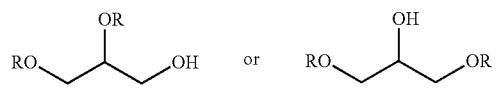

wherein each R is an independently selected acyl group R'—C(O), wherein each R' is a an aliphatic group, independently selected from saturated and unsaturated aliphatic moieties.

As used herein "saturated aliphatic moiety" refers to a branched or unbranched hydrocarbyl group of formula $C_nH_{2n+1}$, wherein n e.g. may be an integer of from 5 to 25.

As used herein "R'—C(O)—" is a moiety of formula

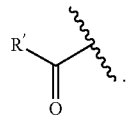

As used herein "saturated aliphatic moiety" refers to a branched or unbranched hydrocarbyl group of formula $C_nH_{2n+1}$, wherein n e.g. may be an integer of from 5 to 25.

As used herein "unsaturated aliphatic moiety" refers to a branched or unbranched hydrocarbyl group of formula $C_nH_{2(n-p)+1}$ containing n carbon atoms and p double bonds, wherein n e.g. may be an integer of from 5 to 25, and p e.g. may be an integer of from 1 to 3, and wherein any two double bonds are separated by at least a methylene group (—$CH_2$—).

As used herein, a "citric acid ester" refers to monoesterified, diesterified or triesterified citric acid, for example of formulas:

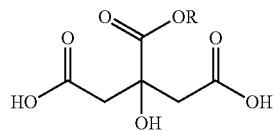

monoesterified citric acid

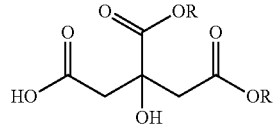

diesterified citric acid

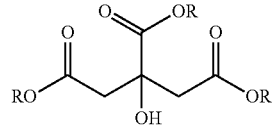

triesterified citric acid

As used herein with regard to citric acid, "monoesterified" means a citric acid molecule having only one carboxylic function esterified, i.e. a citric acid molecule of formula (a) or (b)

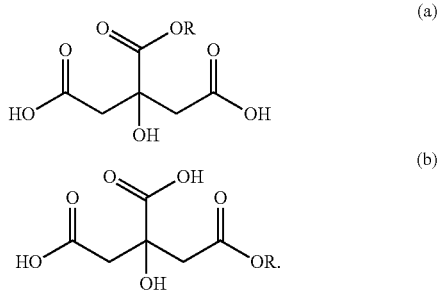

(a)

(b)

As used herein "mixture of citric acid esters of mono- and/or diglyceride" includes mixtures of mono-, di- and triesterified citric acid esters of one or more mono- and/or diglycerides, such as the commercially available Citrems.

The term "basifying agent" as used herein refers to an agent capable of raising the pH of an aqueous solution, e.g. an agent selected from metal hydroxides and carbonates, e.g. sodium carbonate and potassium carbonate.

As used herein, and unless otherwise indicated or apparent from the context, the term "Fe ions" refers to ions of the element iron (Fe) in oxidation state (II) (i.e. $Fe^{2+}$) or (III) (i.e. $Fe^{3+}$), preferably in the oxidation state (III).

Reference to various publications is made herein and the contents of these publications are incorporated herein by reference.

A first aspect relates to a composition comprising (i) Fe ions; and (ii) a citric acid ester of mono- and/or diglyceride or a mixture of citric acid esters of mono- and/or diglyceride. Component (i)

Component (i) comprises a Fe salt of a C8 to C24 fatty acid. Preferably, the Fe (iron) is Fe(III), but some iron may also be present as Fe(II). In some embodiments, the iron is present as Fe(III). In some embodiments, the iron is present as Fe(III) and Fe(II).

The Fe salt of a C8 to C24 fatty acid is an iron salt of a fatty acid, such as an iron salt of a C8 to C22 fatty acid, or C8 to C20 fatty acid, or C8 to C18 fatty acid, or C10 to C18 fatty acid, or C12 to C18 fatty acid, or C14 to C8 fatty acid or a hydrate of any of these salts. The C8 to C24 fatty acid normally is an edible fatty acid.

In some embodiments, component (i) an iron salt of a C10 to C24 fatty acid, or C10 to C22 fatty acid, or C10 to C20 fatty acid, or C10 to C18 fatty acid. In some embodiments, component (i) an iron salt of a C12 to C24 fatty acid, or C12 to C22 fatty acid, or C12 to C20 fatty acid, or C12 to C18 fatty acid. In some embodiments, component (i) an iron salt of a C14 to C24 fatty acid, or C14 to C22 fatty acid, or C14 to C20 fatty acid, or C14 to C18 fatty acid. In some embodiments, component (i) an iron salt of a C16 to C24 fatty acid, or C16 to C22 fatty acid, or C16 to C20 fatty acid, or e.g. a C18 fatty acid. In some of these embodiments the fatty acid is saturated.

In some embodiments, component (i) comprises an iron salt of a fatty acid a salt of a fatty acid as mentioned in Tables 1 and 2. Iron salts of fatty acids are commercially available or may be prepared e.g. according to any of the processes disclosed in U.S. Pat. No. 5,434,277 or in U.S. Pat. No. 7,705,169. In some embodiments, component (i) comprises iron stearate, e.g. $Fe_3O(stearate)_6$.

In some particular embodiments, the C8 to C24 fatty acid iron salt includes a cation of formula (A)

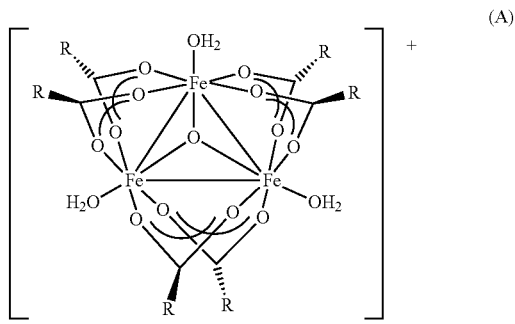

(A)

wherein each R is an independently selected aliphatic moiety, and at least one R, preferably each R, corresponds to the aliphatic chain of a C8 to C24 fatty acid. For example, in some embodiments, the iron salt of formula (A) is a salt wherein each R is selected from the aliphatic chain of lauric acid, myristic acid, palmitic acid, or stearic acid. In some of these embodiments, each R is selected from the aliphatic (C11) chain of lauric acid. In some other of these embodiments, each R is selected from the aliphatic (C13) chain of myristic acid. In some other of these embodiments, each R is selected from the aliphatic (C15) chain of palmitic acid. In some other of these embodiments, each R is selected from the aliphatic (C17) chain of stearic acid.

It is noted that the complex cation of formula (A) may be represented by the general molecular formula $Fe_3O(RC(O)O)_6(H_2O)_3{}^+$. A salt containing the cation of formula (A) therefore may be written as a salt of formula $[Fe_3O(RC(O)O)_6(H_2O)_3{}^+]_nL^{n-}$, wherein n is an integer of at least 1, e.g. n i 1 or 2, and $L^{n-}$ is a moiety carrying n negative charges.

In some embodiments, $L^{n-}$ is a deprotonated C8 to C24 fatty acid, $R_ACOO^-$, i.e. the salt is a complex salt that may be represented by the molecular formula $[Fe_3O(RC(O)O)_6(H_2O)_3]^+R_AC(O)O^{n-}$ (alternatively written: $R_AC(O)O[Fe_3O(RC(O)O)_6(H_2O)_3]$).

In some of these embodiments, $R_A$ and each R are aliphatic moieties corresponding to a C8 to C24 fatty acid as mentioned herein above, e.g. $R_A$ and each R are aliphatic moieties corresponding to a C8 to C20 aliphatic acid, or C10 to C20 aliphatic acid, or C12 to C20 aliphatic acid, e.g. a C8 to C18 aliphatic acid. In some embodiments, the aliphatic acid is saturated. In some embodiments, all R are the same, and $R_A$ is the same as R or is different. In some embodiments, $R_A$ and all R are the same.

In some embodiments, $R_A$ and each R correspond to the aliphatic moieties of fatty acids independently selected from any of the acids shown in Tables 1 or 2, e.g. all correspond to lauric acid, myristic acid, palmitic acid or stearic acid. In some embodiments, $R_A$ and all R correspond to stearic acid (i.e. $R_A$ and each R are n-heptadecyl). In some embodiments, $R_A$ and all R correspond to stearic acid (i.e. $R_A$ and each R are n-heptadecyl). In some embodiments, $R_A$ and all R correspond to lauric acid (i.e. $R_A$ and each R are n-undecyl).

In some other embodiments, $L^{n-}$ is $SO_4{}^{2-}$, i.e. the salt may be represented by the molecular formula $[Fe_3O(RC(O)O)_6(H_2O)_3{}^+]_2SO_4{}^{2-}$ (or $[Fe_3O(RC(O)O)_6(H_2O)_3]_2SO_4$).

In a salt of formula $[Fe_3O(RC(O)O)_6(H_2O)_3{}^+]_nL^{n-}$, each R is an independently selected moiety corresponding to the aliphatic chain of a C8 to C24 fatty acid as mentioned herein above. In some embodiments, all R are the same.

In some further embodiments, component (i) is provided as a hydrate of a salt of formula $[Fe_3O(RC(O)O)_6(H_2O)_3^+]_nL^{n-}$, e.g. a hydrate including 1 or 2 water molecules. Any reference to an iron salt of a C8 to C24 fatty acid therefore also should be understood as a reference to a hydrate thereof, unless otherwise specified herein or apparent from the context.

Component (ii)

The component (ii) comprises a citric acid ester of mono- and/or diglyceride or a mixture of citric acid esters of mono- and/or diglyceride. In some embodiments, component (ii) is a mixture of citric acid esters of mono- and/or diglyceride, e.g. a commercially available mixture, of the type referred to as Citrem.

Herein below, the "citric acid ester of mono- and/or diglyceride or a mixture of citric acid esters of mono- and/or diglyceride" may be collectively referred to as "citric acid ester component" or "component (ii)". A citric acid ester of mono- and/or diglyceride as used herein may be represented by formula (I)

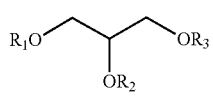

(I)

wherein one of $R_1$, $R_2$ and $R_3$ represents a citric acid moiety, and the two others represent hydrogen (H) or a fatty acid moiety of formula R'—C(O)—. An illustrating (but non-limiting) example of a compound of formula (I) wherein $R_1$ is a (monoesterified) citric acid moiety, is as represented by formula (I')

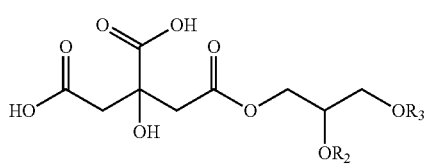

(I')

wherein $R_2$ and $R_3$ are independently selected from H and a fatty acid residue R'—C(O)—.

For the avoidance of doubt, it is pointed out that in a diglyceride, where both $R_2$ and $R_3$ (or $R_1$ and $R_3$) are residues R'—C(O)— of a fatty acid R'—C(O)OH, these residues may be different or same.

The fatty acid R'—C(O)OH (corresponding to the fatty acid residue R'—C(O)—) may be of any origin, e.g. derived from a vegetable oil, and may be e.g. saturated, mono-unsaturated, di-unsaturated, or tri-unsaturated, and normally is an edible fatty acid. In some embodiments, the fatty acid is unsaturated, e.g. mono-unsaturated, di-unsaturated, or tri-unsaturated. In some embodiments, the fatty acid is di-unsaturated. In some other embodiments, the fatty acid is mono-unsaturated. The fatty acid preferably has an unbranched (linear) chain, and contains from e.g. 8 to 24 carbon atoms. In some embodiments, the number of carbon atoms in the fatty acid is at least 10, at least 12, at least 14, or at least 16. In some embodiments, the number of carbon atoms in the fatty acid is at most 24, at most 22, at most 20 or at most 18. In some embodiments, a saturated acid is selected from any one of the fatty acids indicated in Table 1, where C:D is the ratio of the total amount of carbon atoms of the fatty acid and its number of carbon-carbon double bonds.

TABLE 1

| Common name | Chemical formula | C:D |
|---|---|---|
| Caprylic acid | $CH_3(CH_2)_6COOH$ | 8:0 |
| Capric acid | $CH_3(CH_2)_8COOH$ | 10:0 |
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |

In some embodiments, a saturated fatty acid R'—C(O) OH is selected from fatty acids having from 8 to 24 carbon atoms, or from 8 to 22 carbon atoms, or from 8 to 20 carbon atoms, or from 8 to 18 carbon atoms, or from 8 to 16 carbon atoms or from 8 to 14 carbon atoms. In some embodiments, a saturated acid is selected from fatty acids having from 10 to 24 carbon atoms, or from 10 to 22 carbon atoms, or from 10 to 20 carbon atoms, or from 10 to 18 carbon atoms, or from 10 to 16 carbon atoms or from 10 to 14 carbon atoms. In some embodiments, a saturated acid R'—C(O) OH is selected from fatty acids having from 12 to 24 carbon atoms, or from 12 to 22 carbon atoms, or from 12 to 20 carbon atoms, or from 12 to 18 carbon atoms, or from 12 to 16 carbon atoms. In some embodiments, a saturated acid R'—C(O) OH is selected from fatty acids having from 14 to 24 carbon atoms, or from 14 to 22 carbon atoms, or from 14 to 20 carbon atoms, or from 14 to 18 carbon atoms.

Some examples of unsaturated fatty acids that may form the fatty acid residue R'—C(O)— are indicated in Table 2, where C:D is the ratio of the total amount of carbon atoms of the fatty acid and its number of carbon-carbon double bonds.

TABLE 2

| Common name | Chemical formula | C:D |
|---|---|---|
| Myristoleic acid | 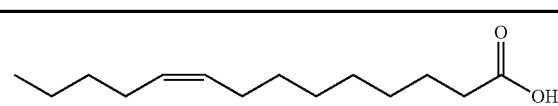 | 14:1 |
| Palmitoleic acid | 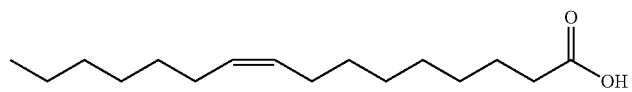 [SMILES: CCCCCC/C=C\CCCCCCCC(=O)O] | 16:1 |

TABLE 2-continued

| Common name | Chemical formula | C:D |
| --- | --- | --- |
| Oleic acid | | 18:1 |
| Elaidic acid | | 18:1 |
| Vaccenic acid | | 18:1 |
| Linoleic acid | | 18:2 |
| Linoelaidic acid | | 18:2 |
| α-Linolenic acid | | 18:3 |
| Arachidonic acid | | 20:4 |
| Eicosapentaenoic acid* | | 20:5 |
| Erucic acid | | 22:1 |
| Docosahexaenoic acid** | | 22:6 |

*IUPAC name: (5Z,8Z,11Z,14Z,17Z)-5,8,11,14,17-icosapentaenoic acid
**IUPAC name: (4Z,7Z,10Z,13Z,16Z,19Z)-docosa-4,7,10,13,16,19-hexaenoic acid In some embodiments, an unsaturated fatty acid R'—C(O)OH has a number of carbon atoms ranging from 10 to 24, e.g. from 10 to 22, or from 10 to 20, or from 10 to 18. In some embodiments, the unsaturated fatty acid has a number of carbon atoms ranging from 12 to 24, e.g. from 12 to 22, or from 12 to 20, or from 12 to 18. In some embodiments, an unsaturated fatty acid has a number of carbon atoms ranging from 14 to 24, e.g. from 14 to 22, or from 14 to 20, or from 14 to 18. In some embodiments, an unsaturated fatty acid has from 16 to 24 carbon atoms, or from 16 to 22 carbon atoms, e.g. from 16 to 20 carbon atoms, e.g. 16 or 18 carbon atoms.

In some embodiments, an unsaturated fatty acid has a number of carbon atoms as indicated herein above and 1-5 carbon-carbon double bonds, e.g. 1-4 carbon-carbon double bonds, or 1-3 carbon-carbon double bonds, e.g. 1 or 2 carbon-carbon double bonds. In some embodiments, an unsaturated fatty acid is mono-unsaturated (i.e. it has one (1) carbon-carbon double bond). In some embodiments, an unsaturated fatty acid is diunsaturated (i.e. it has two (2) carbon-carbon double bonds). In some embodiments, a fatty acid is a C18 fatty acid, e.g. a C18 mono- or diunsaturated fatty acid, in particular a C18 monounsaturated fatty acid. In some particular embodiments, a fatty acid is a C14-C24 mono- or diunsaturated fatty acid, e.g. a C14-C22 mono- or diunsaturated fatty acid, or a C16-C22 mono- or diunsaturated fatty acid, e.g. a C16-C20 mono- or diunsaturated fatty acid.

Citric acid esters of mono- and/or diglycerides (Citrem, E number: E472c; FDA-CFR number: 172.832) are used as additives and emulsifiers in the food industry and are considered as a food substance of very low toxicity. Thus, Citrem has been described as "generally recognized as safe" (GRAS) for direct addition to foods (Food Funct. 2015, 5, 1409, and references cited therein). Citrems may be purchased from various suppliers to in particular the food processing industry, such as Acatris (www.acatris.com) or Danisco (www.danisco.com).

General methods for the preparation and characterization of citric acid esters of mono- and/or diglycerides are well-known and were described as early as in the U.S. Pat. No. 2,938,027, issued on May 24, 1960.

According to one embodiment, the composition disclosed herein comprises a mixture of citric acid esters of mono- and/or diglycerides of the type generally referred to as Citrem. The composition of the present invention comprises in particular mono-esterified citric acid of mono- and/or diglycerides. It should be noted, though, that di- and tri- esters of citric acid may also be present in the composition of the invention. Preferably, component (ii) comprises a major portion of monoesterified citric acid, i.e. the fraction (portion) of monoesterified citric acid molecules is higher than the portion of diesterified citric acid molecules and higher than the portion of triesterified citric acid molecules. In some embodiments, at least 35% by weight of component (ii) is monoesterified citric acid (including mixtures of monoesterified acid). In some embodiments, at least 50% by weight of component (ii) is monoesterified citric acid. In some embodiments, at least 60% by weight of component (ii) is monoesterified citric acid. In some embodiments, at least 70% by weight of component (ii) is monoesterified citric acid. In some embodiments, at least 80% by weight of component (ii) is monoesterified citric acid. In some embodiments, at least 90% by weight of component (ii) is monoesterified citric acid. In some embodiments, at least 95% by weight of component (ii) is monoesterified citric acid.

Normally, component (ii) will comprise a blend (mixture) of various citric acid esters of mono- and diglycerides. In some preferable embodiments, the blend comprises mainly mono-esterified citric acid esters of mono- and/or diglycerides. In some embodiments, the fatty acid moieties of the mono- and/or diglycerides are derived from unsaturated fatty acids, as mentioned herein above. For example, in some embodiments, component (ii) comprises a major portion of citric acid esters of mono- and/or diglycerides of edible mono-unsaturated C8-C24 fatty acids, e.g. edible mono-unsaturated C16-C20 fatty acids. An example of a citric acid ester of mono- and/or diglyceride that may suitably be present in a composition of the invention is dioleoylglycerol citrate.

Component (iii)

In some embodiments, a composition is provided, comprising, in addition to the above described components (i) and (ii), a component (iii), which is a fatty acid or a mixture of fatty acids. The fatty acid component (iii) may comprise one or more fatty acids, e.g. one or more of the fatty acids mentioned herein above (cf. Tables 1 and 2). Preferably component (iii) comprises a saturated fatty acid as defined herein above, e.g. one containing 10-24 carbon atoms, or 12-24 carbon atoms, or 14-24 carbon atoms, e.g. 16-22 carbon atoms, or 16-20 carbon atoms. In some embodiments, the fatty acid component (iii) is stearic acid. In some embodiments, the fatty acid component (iii) comprises stearic acid. In some embodiments, the fatty acid component (iii) comprises a mixture of fatty acids, e.g. a mixture of fatty acids as defined herein above, e.g. a mixture of saturated fatty acids or a mixture of saturated and unsaturated fatty acids. In some embodiments, the fatty acid component comprises at least 2 different fatty acids, e.g. at least 2 different fatty acids selected from those mentioned herein above (cf. Tables 1 and 2).

In some embodiments, the fatty acid component (iii) comprises at least 2 different fatty acids containing 10-24 carbon atoms each, or 12-24 carbon atoms, or 14-24 carbon atoms, e.g. 14-22 carbon atoms, or 14-20 carbon atoms. In some embodiments, the fatty acid component (iii) comprises stearic acid and at least one further fatty acid, e.g. a fatty acid containing 8-24 carbon atoms, or 8-22 carbon atoms, or 8-20 carbon atoms, e.g. 8-18 carbon atoms, or 8-16 carbon atoms, or 8-14 carbon atoms. In some of these embodiments, the further fatty acid is a saturated fatty acid, e.g. myristic acid.

For example, in some embodiments, component (iii) comprises a first fatty acid, such as stearic acid, and a second fatty acid, e.g. a second saturated fatty acid, such as a second fatty acid as defined herein above, e.g. myristic acid, in a molar ratio of the first fatty acid to the second fatty acid of 20:1 to 1:20, from 10:1 to 1:10, or from 5:1 to 1:5, from 4:1 to 1:4, from 3:1 to 1:3, from 2:1 to 1:2, from 1.5:1 to 1:1.5, e.g. about 1:1.

The particular weight ratio of components (ii) and (iii) in the inventive composition may vary within e.g. a range of from 50:1 to 1:1. In some embodiments, the composition of the invention comprises component (ii) and component (iii) in a weight ratio of component (ii) to (iii) of from 20:1 to 1:1, e.g. from 10:1 to 1:1; from 8:1 to 1:1; from 6:1 to 1:1; or from 5:1 to 1:1. In some embodiments, the composition of the invention comprises component (ii) and component (iii) in a weight ratio of component (ii) to (iii) of from 20:1 to 2:1; from 10:1 to 2:1: from 8:1 to 2:1; from 6:1 to 2:1; or from 5:1 to 2:1. In some embodiments, the composition of the invention comprises component (ii) and component (iii) in a weight ratio of component (ii) to (iii) of from 20:1 to 3:1; from 10:1 to 3:1: from 8:1 to 3:1; from 6:1 to 3:1; or from 5:1 to 3:1. In some embodiments, the composition of the invention comprises component (ii) and component (iii) in a weight ratio of component (ii) to (iii) of from 20:1 to 4:1; from 10:1 to 4:1: from 8:1 to 4:1; from 6:1 to 4:1; or from 5:1 to 4:1.

In some embodiments, e.g. in embodiments where component (i) comprises an iron salt of fatty acid or a mixture of iron salts of fatty acids, the inventive composition may comprise component (ii) and component (i) in a weight ratio of component (ii) to (i) of, for example, from 20:1 to 1:1, from 10:1 to 1:1; from 8:1 to 1:1; from 6:1 to 1:1; or from 5:1 to 1:1. In some embodiments, the composition of the invention comprises component (ii) and component (i) in a weight ratio of component (ii) to (i) of from 20:1 to 2:1; from 10:1 to 2:1: from 8:1 to 2:1; from 6:1 to 2:1; or from 5:1 to 2:1. In some embodiments, the composition of the invention comprises component (ii) and component (i) in a weight ratio of component (ii) to (i) of from 20:1 to 3:1; from 10:1 to 3:1: from 8:1 to 3:1; from 6:1 to 3:1; or from 5:1 to 3:1. In some embodiments, the composition of the invention comprises component (ii) and component (i) in a weight ratio of component (ii) to (i) of from 20:1 to 4:1; from 10:1 to 4:1: from 8:1 to 4:1; from 6:1 to 4:1; or from 5:1 to 4:1.

In some embodiments, e.g. in embodiments where component (i) comprises an iron salt of fatty acid or a mixture of iron salts of fatty acids, the weight ratio of component (i) to component (iii) may range from 20:1 to 1:20, from 10:1 to 1:10, from 5:1 to 1:5, from 4:1 to 1:4, from 3:1 to 1:3, or from 2:1 to 1:2, or from 1.5:1 to 1:1.5.

In some embodiments, a composition of the invention is comprised of from about 5 to 50% by weight of component (i), from about 50 to 95% by weight of component (ii) and up to about 20% by weight of component (iii). In some embodiments, a composition is comprised of from 5 to 20% by weight of component (i), from 60 to 95% by weight of component (ii) and up to 20% by weight of component (iii); e.g. about 5 to 20% of component (i), about 60 to 90% of component (ii) and about 5 to 20% of component (iii), or about 10 to 20% of component (i), about 60 to 80% of component (ii) and about 10 to 20% of component (iii). In some embodiments, a composition of the invention is comprised of about 15 to about 20% by weight of component (i), about 60 to about 70% by weight of component (ii), and about 15 to 20% by weight of component (iii).

It is pointed out that the ingredients of the composition of the invention are selected from compounds that are acceptable for ingestion (edible) at the intended amounts corresponding to e.g. daily ingestion of the inventive composition. In embodiments wherein the composition is intended for use in therapy, the ingredients of the composition are selected from pharmaceutically acceptable compounds.

Method of Preparation

Also provided herein is a method for the preparation of an iron containing composition, by
- admixing an iron salt as defined herein, a citric acid ester of mono- and/or diglyceride or a mixture of citric acid esters of mono and/or diglyceride, and optionally one or more fatty acids or fatty acid salts;
- optionally adding a preferably small amount of water and optionally adding a basifying agent; and
- processing the mixture to obtain a stable dispersion.

The basifying agent e.g. is a carbonate, e.g. a metal carbonate such as potassium carbonate ($K_2CO_3$), or any other component capable of providing hydroxyl ions in an aqueous phase.

The processing of the mixture to obtain a stable dispersion e.g. may include one or more sonications, e.g. one or more sonications before adding the water and one or more sonications after adding the water and the basifying agent.

Use of one or more emulsifiers to aid in forming a stable dispersion is also contemplated. It is considered well within the knowledge of the person of ordinary skill in the art to select a proper emulsifying agent, for example an emulsifier having a HLB value of 8 to 20, e.g. from 8 to 15.

In some embodiments, the method comprises admixing an iron salt as defined herein, and a citric acid ester of mono- and/or diglyceride, e.g. a monoesterified citric acid ester of mono- or diglyceride, optionally submitting the mixture to treatment by ultrasound (sonication), optionally submitting the mixture to heating, e.g. at a temperature of from 40° C. to 80° C., or from 50° C. to 70° C., followed by addition of a small amount of water and a basifying agent, e.g. a carbonate salt, such as $K_2CO_3$, optionally followed by a further sonication. In some preferred embodiments, a fatty acid, such as a saturated fatty acid, e.g. stearic acid, is added to the mixture, e.g. before the first sonication.

The iron salt is salt of a C8 to C24 fatty acid as mentioned herein. In some embodiments, the iron salt is an iron salt of a C8 to C18 fatty acid, or C8 to C16 fatty acid, or C8 to C14 fatty acid, e.g. selected from any of the fatty acids as mentioned herein above (cf. e.g. Tables 1 and 2).

The iron salt preferably is a Fe(III) salt. In some embodiments, the iron salt is a Fe(II) salt of a fatty acid, such as a Fe(II) salt of a C8 to C18 fatty acid, or C8 to C16 fatty acid, or C8 to C14 fatty acid, e.g. selected from any of the fatty acids as mentioned herein above (cf. e.g. Tables 1 and 2).

In some embodiments, component (i) comprises Fe(II) and/or Fe(III) salts of one or more fatty acids, such as Fe(II) and/or Fe(III) salts of one or more C8 to C18 fatty acids, or C8 to C16 fatty acids, or C8 to C14 fatty acids, e.g. one or more of the fatty acids as mentioned herein above (cf. e.g. Tables 1 and 2).

The citric acid ester of mono- and/or diglyceride component may be any of the commercially available Citrems, or may be prepared by esterification of glycerol with citric acid and one or more fatty acids, or by reaction of a mixture of mono- and diglycerides with citric acid. It should be realized that the citric ester of mono- and/or diglyceride as referred to herein normally therefore will be a mixture of various reaction products from such a reaction, including e.g. various positional isomers.

The composition of the invention may be administered orally, and may be included in a pharmaceutical formulation, a nutritional supplement, a liquid or solid food composition, a drinkable formulation, etc., e.g. as a dispersion of the composition according to the invention in a suitable vehicle, e.g. water, or a viscous liquid phase, e.g. a gel. In some embodiments, the formulation is provided in dried form, e.g. as a powder that may be filled into a capsule or incorporated into a food. In some embodiments, the formulation is provided as a dispersion of the composition according to the invention in a suitable vehicle, e.g. water, or a viscous liquid phase, e.g. a gel. In some embodiments, the formulation is provided as a powder of granules.

Pharmaceutical Formulation

Provided herein is a pharmaceutical formulation comprising the inventive composition, preferably a formulation for oral administration, such as a liquid formulation, or a gel capsule for oral administration, e.g. a hard capsule or a soft elastic (gelatin) capsule, containing the inventive dispersion and optionally also one or more pharmaceutically acceptable excipients, such as a preservative, a viscosity agent, an emulsifying agent, a thickener etc; and optionally also one or more further active ingredients.

In some embodiments, the formulation is provided as a dispersion of the composition according to the invention in a suitable vehicle, e.g. water, or a viscous liquid phase, e.g. a gel. In some embodiments, the formulation is provided in dried form, e.g. as a powder that may be filled into a capsule.

An emulsifying agent that may be used in the formulation e.g. may be derived from a natural source, such as acacia, tragacanth, alginate, xanthan, pectin and lecithin. A viscosity agent e.g. may be a hydrophilic colloid, such as acacia, tragacanth, alginate, xanthan, pectin, a cellulose derivative, such as methylcellulose, hydroxypropylmethylcellulose, or sodium carboxymethylcellulose, or e.g. a carbomer polymer. A preservative e.g. may be ascorbic acid, benzoic acid, or an ester of p-hydroxybenzoic acid.

For example, the formulation may comprise the inventive composition in an amount of from 1 to 99% by weight of the formulation, e.g. from 5 to 95% by weight, or from 10 to 90% by weight, or from 20 to 80% by weight, the remainder comprising one or more excipients.

In some embodiments, a formulation as provided herein may comprise iron in the form of an iron salt as defined herein in an amount of about 0.05% by weight, about 0.1% by weight, e.g. about 0.2% by weight, about 0.5% by weight, about 1% by weight, about 1.2% by weight, about 1.3% by weight, about 1.4% by weight, about 1.5% by weight, about 2% by weight, about 3% by weight, or about 5% by weight, based on the total weight of the formulation. In some embodiments, the formulation comprises iron in an amount ranging from about 0.05 to 5% by weight, 0.1 to 5% by weight, 0.2 to 5% by weight, 0.5 to 5% by weight, 1.0 to 5% by weight, 1.2 to 5% by weight, 1.3 to 5% by weight, 1.4 to 5% by weight, 1.5 to 5% by weight, 2 to 5% by weight, or 3 to 5% by weight, based on the total weight of the formulation. In some embodiments, the formulation comprises iron in an amount ranging from about 0.05 to 3% by weight, 0.1 to 3% by weight, 0.2 to 3% by weight, 0.5 to 3% by weight, 1.0 to 3% by weight, 1.2 to 3% by weight, 1.3 to 3% by weight, 1.4 to 3% by weight, 1.5 to 3% by weight, or 2 to 3%, based on the total weight of the formulation. In some embodiments, the formulation comprises iron in an amount ranging from about 0.05 to 2% by weight, 0.1 to 2% by weight, 0.2 to 2% by weight, 0.5 to 2% by weight, 1.0 to 2% by weight, 1.2 to 2% by weight, 1.3 to 2% by weight, 1.4 to 2% by weight, or 1.5 to 2% by weight, based on the total weight of the formulation. In some embodiments, the formulation comprises iron in an amount ranging from about 0.05 to 1.5% by weight, 0.1 to 1.5% by weight, 0.2 to 1.5% by weight, 0.5 to 1.5% by weight, 1.0 to 1.5% by weight, 1.2 to 1.5% by weight, 1.3 to 1.5% by weight, or 1.4 to 1.5% by weight, based on the total weight of the formulation. In some embodiments, the formulation comprises iron in an amount ranging from about 0.05 to 1.3% by weight, 0.1 to 1.3% by weight, 0.2 to 1.3% by weight, 0.5 to 1.3% by weight, 1.0 to 1.3% by weight, or 1.2 to 1.3% by weight, based on the total weight of the formulation. In some embodiments, the formulation comprises iron in an amount ranging from about 0.05 to 1.2% by weight, 0.1 to 1.2% by weight, 0.2 to 1.2% by weight, 0.5 to 1.2% by weight, or 1.0 to 1.2% by weight, based on the total weight of the formulation. In some embodiments, the formulation comprises iron in an amount ranging from about 0.05 to 1% by weight, 0.1 to 1% by weight, 0.2 to 1% by weight, or 0.5 to 1% by weight, based on the total weight of the formulation. In some embodiments, the formulation comprises iron in an amount ranging from about 0.05 to 0.5% by weight, 0.1 to 0.5% by weight, or 0.2 to 0.5% by weight, based on the total weight of the formulation.

Preferably the pharmaceutical formulation of the invention is a delayed release formulation, e.g. having an enteric surface coating. In some embodiments, the formulation is a capsule having an enteric coating, allowing for the release of the active ingredients in the intestine. In some embodiments, the formulation of the invention comprises an enteric soft capsule, e.g. as described in WO 2014/140991, or in U.S. Pat. No. 9,775,814, or U.S. Pat. No. 5,330,759.

In some embodiments, the pharmaceutical formulation of the invention is a sustained release formulation. For example, sustained release film-coated capsules are described in WO 2017/075215. In some embodiments, the pharmaceutical formulation of the invention is delayed release formulation allowing for sustained release in the intestine.

Further information on the use and manufacture of pharmaceutical formulations are described e.g. in Remington: The Science and Practice of Pharmacy ($22^{nd}$ edition), Pharmaceutical Press, 2013.

The formulation of the present invention is advantageously used in the treatment of iron deficiency or disorders or diseases related to iron deficiency, such as anaemia, in e.g. fertile women, pregnant women, children, adolescents, elderly etc. Treatment may include administration of a pharmaceutical formulation as disclosed herein, e.g. once or twice a day, continuously or over a time period of from e.g. 1 month to 12 months, or 1 month to 6 months, or until a desired level of blood iron has been reached in the treated subject. A suitable daily dose may comprise from 10 to 70 mg of iron, from 10 to 50 mg of iron, from 10 to 40 mg of iron, from 10 to 30 mg of iron, or from 10 to 20 mg of iron. Treatment also may be prophylactic, e.g. in persons that are susceptible to iron deficiency, such as fertile or pregnant women, vegetarians, people suffering from diseases such as cancer, in particular cancer of the gastrointestinal system, inflammatory bowel disease, anorexia, or chronic inflammation etc., as well as elderly people or people suffering from a loss of appetite, such as due to depression.

In some embodiments, a dietary supplement is provided, comprising the composition of the invention. The formulation and administration form of the dietary supplement generally may be the same as described herein above for the pharmaceutical formulation. For example, the dietary supplement may be provided in the form of a hard or soft gel capsule, or in the form of a dispersion in a liquid vehicle, in a flask accompanied by a dosage spoon or similar and with appropriate dosage instructions. A dietary supplement or pharmaceutical formulation as provided herein additionally may comprise one or more further biologically and/or therapeutically active agents, e.g. a vitamin, such as vitamin A, B, C, D E or K, a mineral, such as Ca, Mg, K, or Se, a plant extract such as resveratrol, lycopene, an extract from spirulina, a phytol etc.

Use in Food

A further aspect is the use of a composition as disclosed herein as a food additive, or in the preparation of a food additive, or in the preparation of a foodstuff. For example, the composition disclosed herein may be incorporated into a foodstuff, e.g. a liquid or jelly like composition, or a viscous liquid, such as a drinkable or edible preparation, together with any other suitable additive, such as thickening agents, emulsifiers, sweeteners, colorants, flavouring agents etc. A further aspect therefore is a food additive or a foodstuff comprising the composition as disclosed herein, e.g. a food intended for nourishing subjects in particular need of iron supplementation, such as elderly, infants, pregnant women, people suffering from a disease condition etc.

The invention is illustrated by the following non-limiting examples.

EXAMPLES

Preparation of Fe Stearate Salt

The salt was prepared following the synthetic method reported by Abrahamson and Lukaski (J. Inorg. Biochem. 54 (1994) 115-130), as follows: Stearic acid (0.6 g) was dissolved in 30 ml of ethanol and was stored overnight in a flask. Next day a pellet of NaOH, dissolved with 1 ml of water (2.13 mM), was added. After slightly heating the flask, 10 ml of water was added to the stearic acid solution. In another flask, $FeSO_4$ (316.9 mg) was dissolved in 10 ml of water and 50 ml of ethanol, mixed under a nitrogen purge and gently heated. The solution of stearic acid was added to the ferrous sulphate solution in 10 ml aliquots over 5 min intervals. Ten millilitres of water were used to rinse remaining traces of stearic acid into the reaction mixture. The reaction mixture changed to a darker colour after adding stearic acid. The heating was turned off after 40 min, and after one hour the nitrogen purge was stopped. The mixture was allowed to stand overnight at room temperature. On the following day the solution was filtered and the traces were washed with 20 ml water. Finally, the filtered solution was placed under a vacuum to dry for 6 hours. The final weight of the iron stearate was 0.632 g (Preparation 1). The preparation was repeated in an identical fashion to give Preparation 2, and was also repeated with an extra final purification, by dissolving of the obtained preparation in ethyl acetate at 70° C., allowing the solution to cool, to form a precipitate, separating the precipitate by centrifugation and drying the obtained product under vacuo overnight, to give Preparation 3, which has the formula $[Fe_3OSt_6(H_2O)_3]_2SO_4(H_2O)_2$.

TABLE 4

| Iron stearate preparation | % C | % H |
|---|---|---|
| Preparation 1 | 65.55 | 10.70 |
| Preparation 2 | 65.47 | 10.86 |

TABLE 4-continued

| Iron stearate preparation | % C | % H |
|---|---|---|
| Preparation 3 | 64.69 | 11.11 |
| Commercial preparation | 66.33 | 11.48 |
| $[Fe_3O(stearate)_6(H_2O)_3]_2SO_4$ | | |
| Theoretical value | 64.71 | 10.86 |

Preparation of $^{59}$Fe Stearate Salt

Stearic acid (0.3 g) was dissolved in 15 ml of ethanol mixed with 500 µl of 2.13 mM NaOH. The labelling of the ferrous sulphate was achieved by dissolving 158.5 mg of FeSO4 in 5 ml of water and adding 2 µl of iron-59 (0.5 MBq) and 25 ml ethanol. The subsequent steps were the same as for the iron stearate salt preparation. The stearic acid mixture was heated and subjected to nitrogen purge. Heat was removed after 40 min of reaction and nitrogen purge continued for a further 20 minutes. The flask was left overnight at room temperature. The filtered solution was dried in a vacuum for 6 hours yielding a final weight of iron-59 stearate of 0.326 g.

Preparation of Fe Laurate Salt

Lauric acid (0.42 g) was dissolved in 30 ml of ethanol and was stored overnight in a flask. Next day a pellet of NaOH, dissolved with 1 ml of water (2.13 mM), was added. After slightly heating the flask, 10 ml of water was added to the lauric acid solution. In another flask, FeSO$_4$ (316.9 mg) was dissolved in 10 ml of water and 50 ml of ethanol, mixed under a nitrogen purge and gently heated. The solution of lauric acid was added to the ferrous sulphate solution in 10 ml aliquots over 5 min intervals. Ten millilitres of water were used to rinse remaining traces of lauric acid into the reaction mixture. The reaction mixture changed to a darker colour after adding lauric acid. The heating was turned off after 40 min, and after one hour the nitrogen purge was stopped. The mixture was allowed to stand overnight at room temperature. On the following day the solution was filtered and the traces were washed with 20 ml water, and the filtered solution was placed under a vacuum to dry for 6 hours. The final weight of the iron laurate was 0.39 g Example 1

A dispersion was prepared using 20 mg of Fe stearate, 80 mg of Citrem (a mixture of citric acid esters of essentially unsaturated mono- and diglycerides), and 20 mg of stearic acid. All the compounds were mixed and sonicated for 30 minutes at 65° C. After sonication, 1 ml of water and 5 mg of K$_2$CO$_3$ were added. A further sonication was run for 30 minutes, the mixture was whirly mixed and exposed to a final sonication for a total of 30 minutes at 65° C. The stability of the obtained dispersion, as prepared and after storage at 4° C. or room temperature (in the dark), was observed by visual observation. There was sedimentation on storage but a relatively stable dispersion was again formed by simply whirly mixing for 30 seconds. Under microscopy virtually all micellar particles were found to be smaller than 1 µM, and the dispersion remained relatively unchanged after 4 weeks of storage at either 4° C. or room temperature.

Example 2

Iron stearate (1.8% by weight), stearic acid (1.8% by weight) and Citrem (7.1% by weight) were admixed and the mixture was allowed to melt by heating at 140° C. for 2 hours in an oven, with vortexing every 30 minutes. At the end of the heating time, an aqueous solution of K$_2$CO$_3$ (0.4% by weight) in 75° C. water (88.9% by weight) was added and the mixture was sonicated in a bath at 75° C. The mixture was allowed to cool down to room temperature while vortex mixing every 15 minutes.

Example 3

A dispersion was prepared using 20 mg of iron stearate, 80 mg of Citrem (a mixture of citric acid esters of essentially unsaturated mono- and diglycerides), and 22.7 mg of potassium stearate. All the compounds were mixed and sonicated for 30 minutes at 65° C. After sonication, 1 ml of water was added. A further sonication was run for 30 minutes, the mixture was whirly mixed and exposed to a final sonication for a total of 30 minutes at 65° C.

The size distribution of this dispersion was investigated in a Morphology 4 (Malvern Instruments, Worcestershire, UK). Bright field illumination was used for the microscope visualization of the dispersion particles with the light intensity calibrated to 70.0±0.2%. The samples were scanned using a 20× objective lens. The scan area was 4.5 mm×4.5 mm. The sample was diluted to 8.5% with H$_2$O and 5 µL placed on a slide. The Instrument accounted about 90,000 particle images with a 90% size of less than 2.42 MM diameter (FIG. 1 and Table 5).

TABLE 5

| Parameter | value |
|---|---|
| Particles counted | 91179 |
| Diameter Minimum (µm) | 0.50 |
| Diameter Maximum (µm) | 18.45 |
| Diameter Mean (µm) | 1.59 |
| Diameter RSD (%) | 52.46 |
| Diameter STDV (µm) | 0.83 |
| Diameter D[n, 0.9] (µm) | 2.42 |
| Diameter D[n, 0.5] (µm) | 1.32 |
| Diameter D[n, 0.1] (µm) | 1.01 |

Example 4

The procedure of EXAMPLE 1 was repeated using $^{59}$Fe stearate instead of Fe stearate. A stable dispersion was obtained.

Example 5

The procedure of EXAMPLE 1 was repeated, using Fe laurate (20 mg) instead of Fe stearate; 80 mg Citrem and 20 mg stearic acid. A stable dispersion was obtained.

Biological Assays

Uptake of Iron by Human Intestinal Caco-2 Cells

Human intestinal Caco-2 cells (passage 40-50) were cultured in Dulbecco's Modified Eagle's Medium (DMEM), with 4500 mg/L glucose, L-glutamine, and sodium bicarbonate, without sodium pyruvate. Fetal calf serum (10%), L-glutamine (1%), penicillin-streptomycin (1%), and Minimum non-essential amino acids (1%) were also added. Cells were grown in a 75 cm$^2$ flask at 37° C. in a humidified atmosphere containing 5% CO$_2$ and 95% air. After confluency in the flask, Caco-2 cells were seeded into six well-plates. The medium in the plates was changed every two days, and after about 14 days, Caco-2 cells were fully differentiated and were supposed to express iron transport proteins. After 14 days of culture, Caco-2 cells were starved overnight with serum free Minimum Essential Eagle Medium. The following day, the cells were washed with Hanks' Balanced Salt Solution (HBSS) and supplemented with an dispersion, prepared as described in Example 1, at an iron concentration of either 50 UM or 100 UM, or 50 UM ferrous ascorbate (1:20, $FeSO_4$ and Na-ascorbate) as a positive control, for 2 hours in HBSS buffer. After the incubation time, the medium was collected in Eppendorf tubes and monitored in a gamma counter. Caco-2 cells were washed with cold Phosphate Buffered Saline pH 7.4, and 0.5 ml of NaOH (0.1 N) was added. Cells were left for 15 minutes in order to achieve lysis, harvested in Eppendorf tubes and monitored in a gamma counter. Afterwards, the concentration of total protein was measured with the Bradford method.

Figure 2:
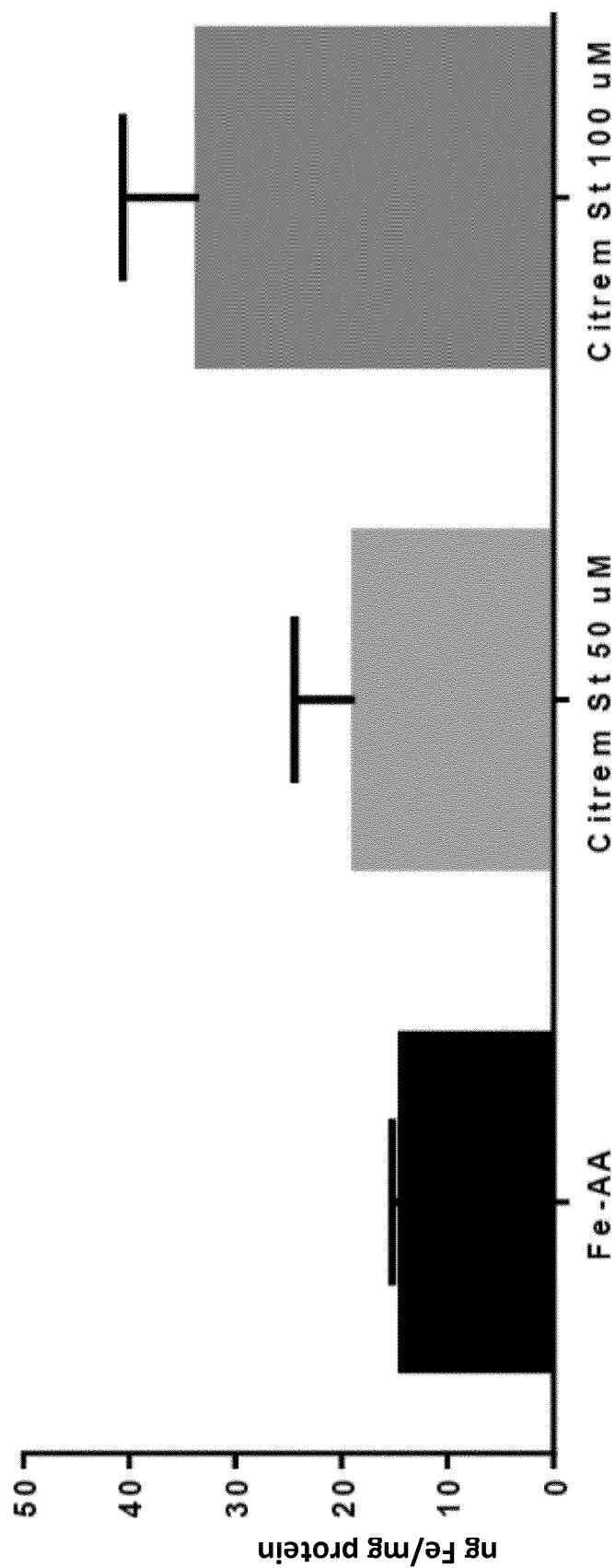
FIG. 2 is a bar chart showing the Caco-2 cell iron uptake, normalized by the total concentration of protein (ng Fe/mg protein), from ferrous ascorbate containing 50 µM Fe (Fe-AA), and from two inventive dispersions, prepared as described in Example 1, containing 50 µM Fe (Citrem St 50 µM) and 100 µM Fe (Citrem St 100 µM), respectively.

The iron uptake in Caco-2 cells, from ferrous ascorbate, and from the inventive formulations, normalized by the total concentration of protein, is represented in FIG. 2.

In Vivo Absorption of Iron in Mouse—$^{59}$Fe-Absorption Study

Figure 3:
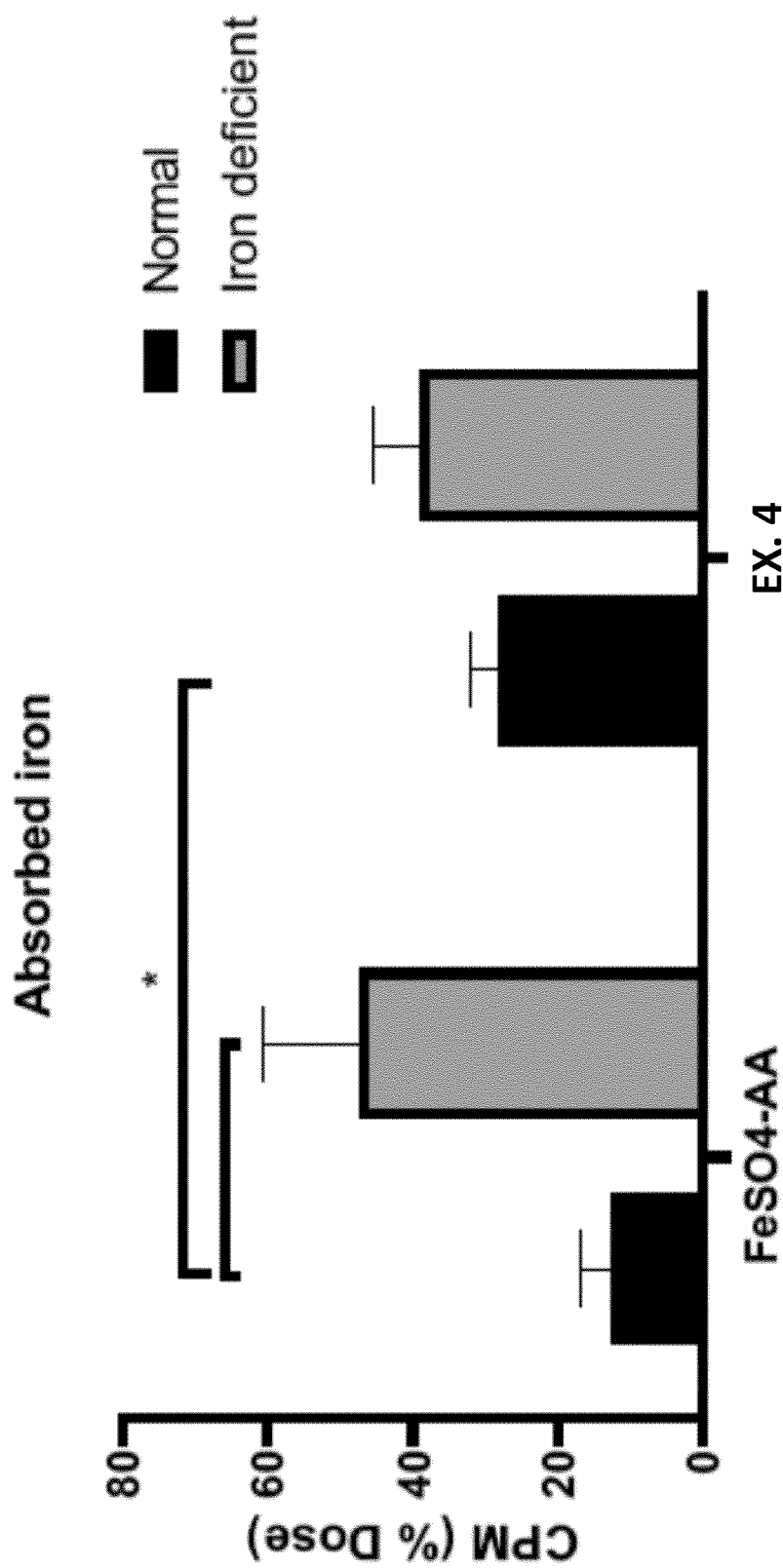
FIG. 3 is a bar chart showing the % of the dose (in CPM) as determined by the measured radioactivity derived from absorbed $^{59}$Fe, in duodenum and carcase of normal or iron deficient mice 4 hours after oral gavage of the mice with ferrous ascorbate ($FeSO_4$:AA 1:1)) ([21 mM $^{59}$Fe], 100 µl) or with Example 4 ([21 mM $^{59}$Fe], 100 µl) (n=6). *(p≤0.05) statistically significant for One-way ANOVA, Tuckey's test.
Figure 4:
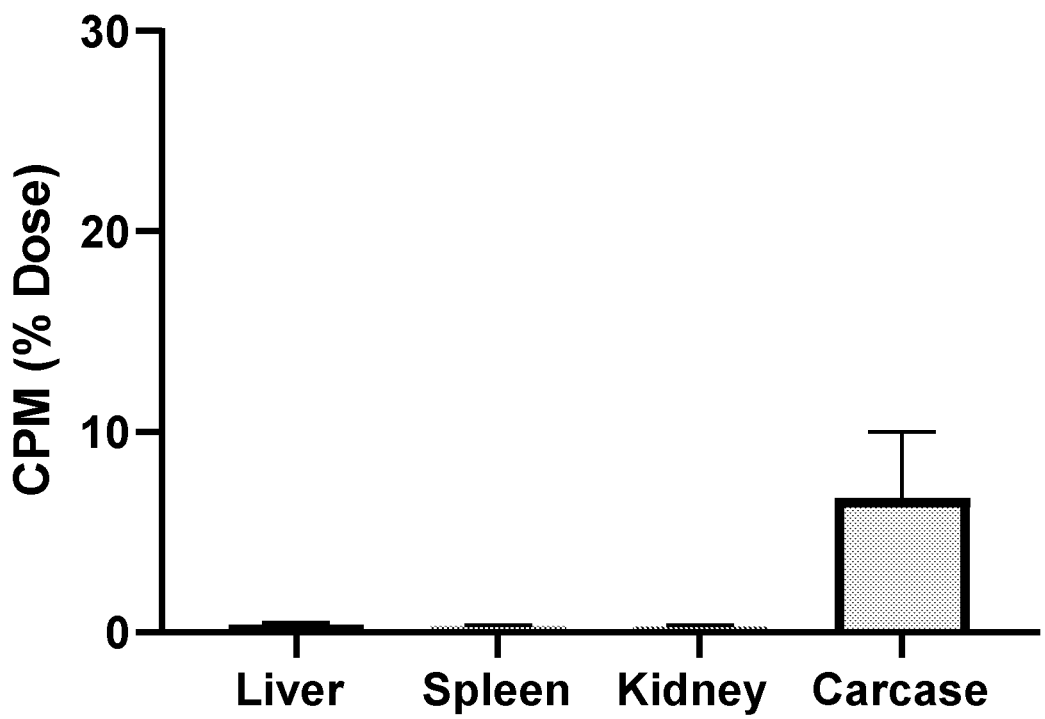
FIG. 4 is a bar chart showing the % of the dose (in CPM) as determined by the measured radioactivity derived from absorbed $^{59}$Fe, in liver, spleen, kidney and carcase of normal diet mice (no iron deficiency) 4 hours after oral gavage of the mice with ferrous ascorbate ($FeSO_4$:AA, 1:1) ([21 mM $^{59}$Fe], 100 µl).
Figure 5:
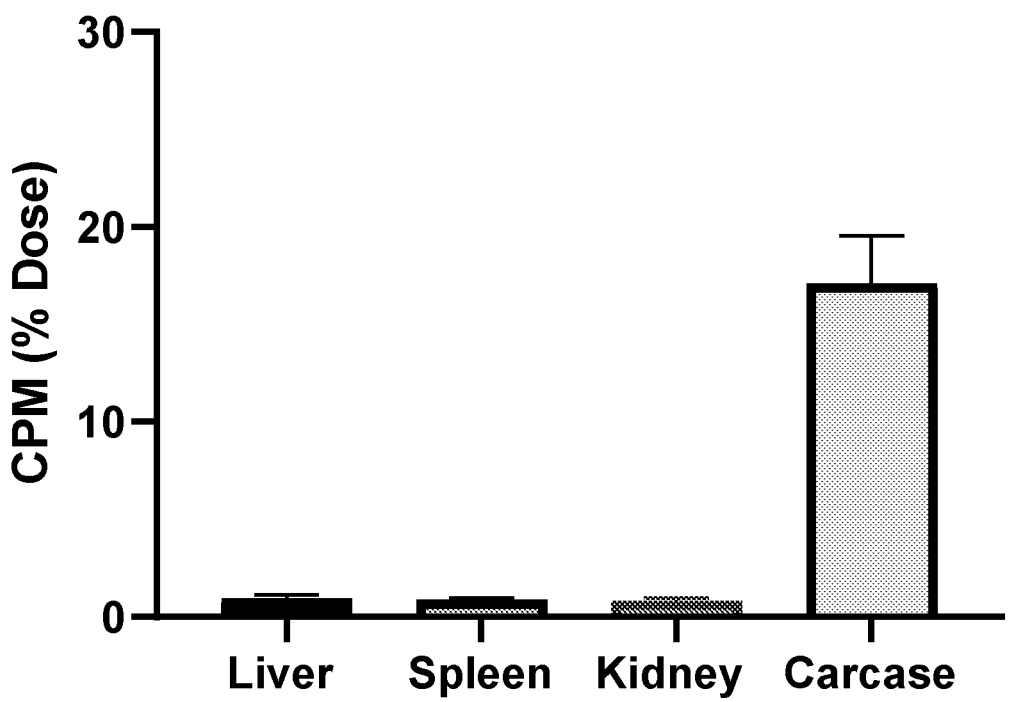
FIG. 5 is a bar chart showing the % of the dose (in CPM) as determined by the measured radioactivity derived from absorbed $^{59}$Fe, in liver, spleen, kidney and carcase of normal diet mice (no iron deficiency) 4 hours after oral gavage of the mice with the formulation of Example 4 ([21 mM $^{59}$Fe], 100 µl).
Figure 6:
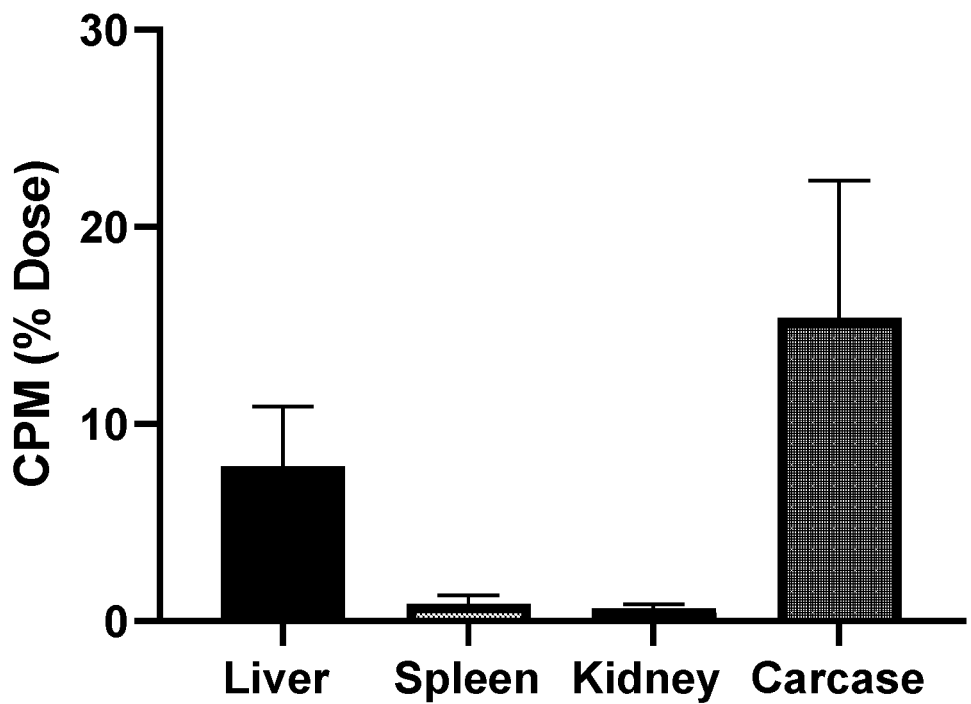
FIG. 6 is a bar chart showing the % of the dose (in CPM) as determined by the measured radioactivity derived from absorbed $^{59}$Fe, in liver, spleen, kidney and carcase of iron deficient mice 4 hours after oral gavage of the mice with ferrous ascorbate ($FeSO_4$:AA, 1:1) ([21 mM $^{59}$Fe], 100 µl).
Figure 7:
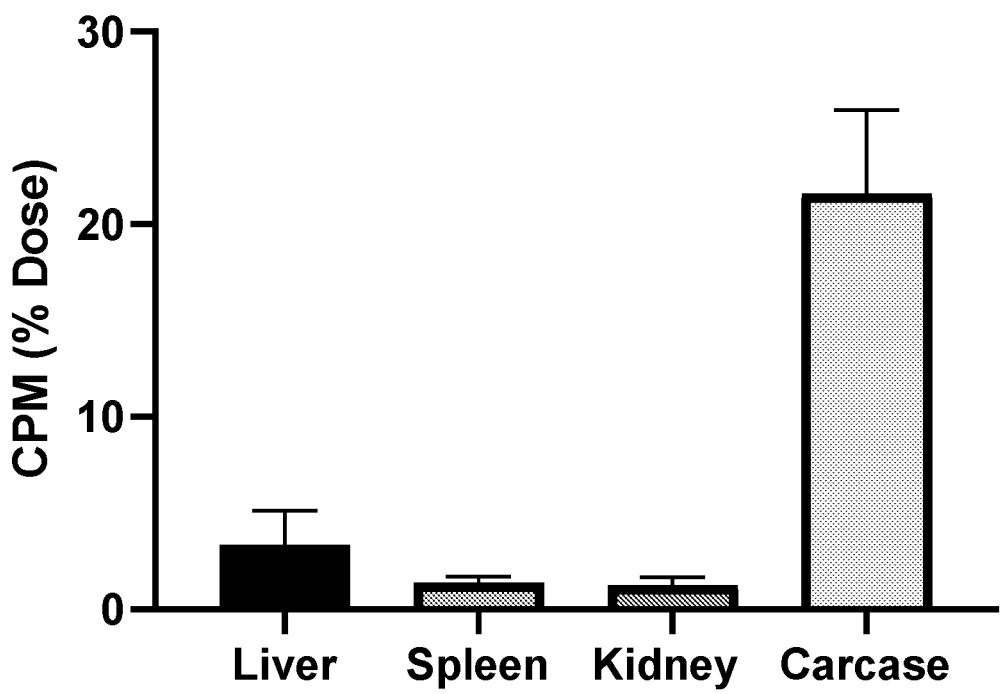
FIG. 7 is a bar chart showing the % of the dose (in CPM) as determined by the measured radioactivity derived from absorbed $^{59}$Fe, in liver, spleen, kidney and carcase of iron deficient mice 4 hours after oral gavage of mice with the formulation of Example 4 ([21 mM $^{59}$Fe], 100 µl).

Anaemic mice were generated using the method of Latunde-Dada et al, J. Nutr. 144 (2014) 1896-902. Mice (3 weeks old) were split into 4 groups (n=6), two groups were fed with normal iron diet (48 mg iron/Kg) and the other two with iron deficient diet (3 mg iron/kg) for 6 weeks. Before the experiment haemoglobin levels were measured to confirm the differences between the normal group and the iron deficient groups. The day before the treatment with $^{59}$Fe labelled iron, all the mice were deprived of food overnight with water ad libitum. Normal (non anaemic) and iron deficient (anaemic) mice were gavaged with either 100 µl of the formulation of Example 4, or with $^{59}FeSO_4$-ascorbic acid (1:1) ([Fe]=21 mM). Four hours after the oral gavage the mice were sacrificed and tissues collected. The results are presented in FIG. 3.

With ferrous sulphate/ascorbic acid there was a marked enhancement of iron absorption in the anaemic mice (FIG. 3) which confirms that the low iron diet did indeed render the animals anaemic (Normal animals 12.6±4% vs anaemic animal, 47.2±13.4%). Significantly, a considerably higher iron absorption (about twice) was observed in the normal animals treated with the inventive composition (28.05±4%), compared to normal animals treated with ferrous sulphate (12.6%). Additionally, the absorption of iron in anaemic mice treated with the formulation of Example 4 was higher 39±6.4%) than in normal mice treated with the formulation of Example 4.

Tissue Distribution

The tissues from the $^{59}$Fe uptake study were used for an investigation of iron distribution (FIGS. 4-7). In the normal animals the majority of the iron is in the "carcase" (probably in blood and lymph). There is however more Fe in liver, spleen and kidney when the formulation of Example 4 is used as the iron source. In the iron deficient mice there was a greater distribution of Fe in the liver when $FeSO_4$ was used as the iron source, but overall the distribution from the two sources was similar.

Haemoglobin Levels in Anaemic Mice after Treatment with Oral Iron

Figure 8:
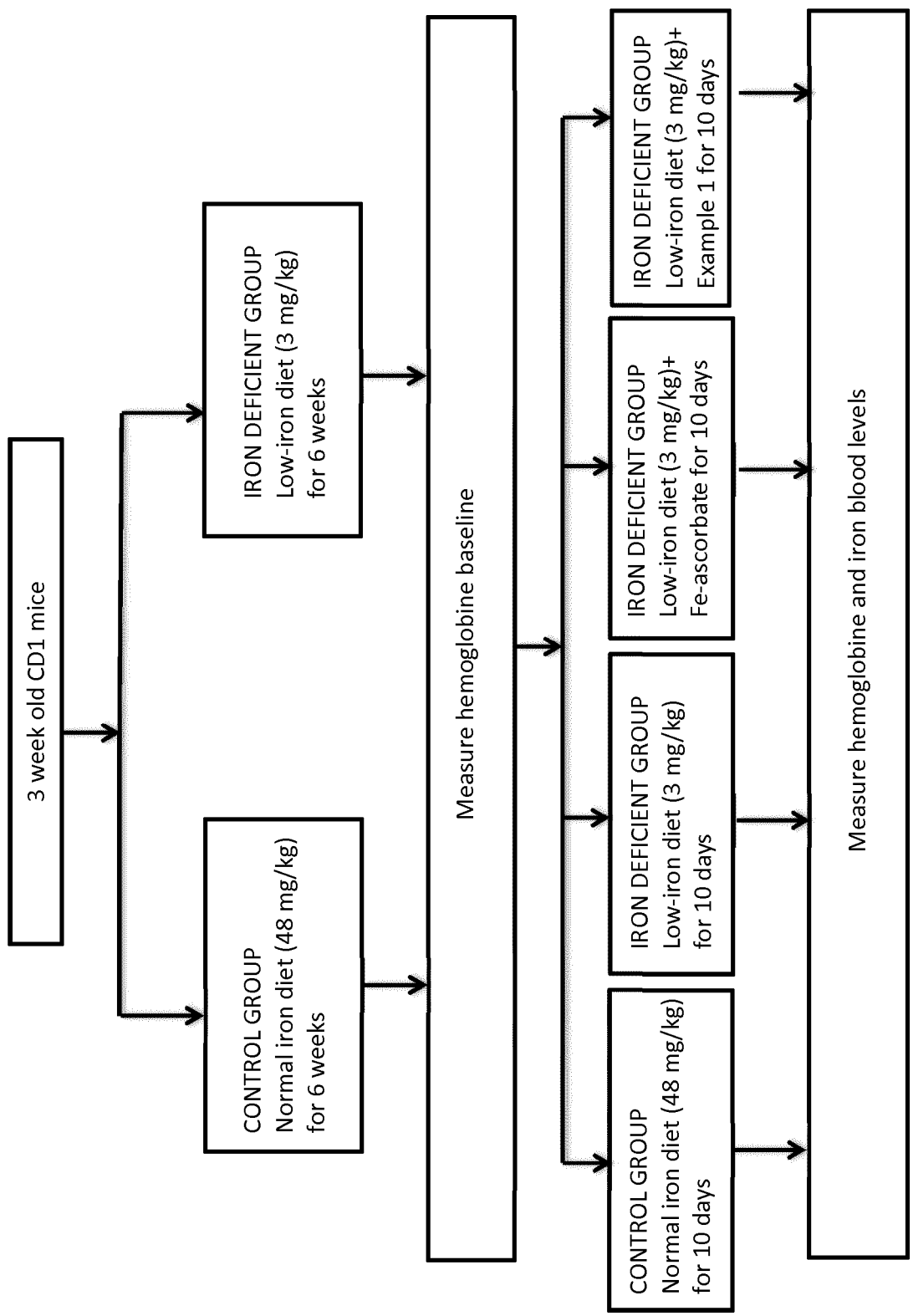
FIG. 8 is a schema showing design of haemoglobin repletion experiment.
Figure 9:
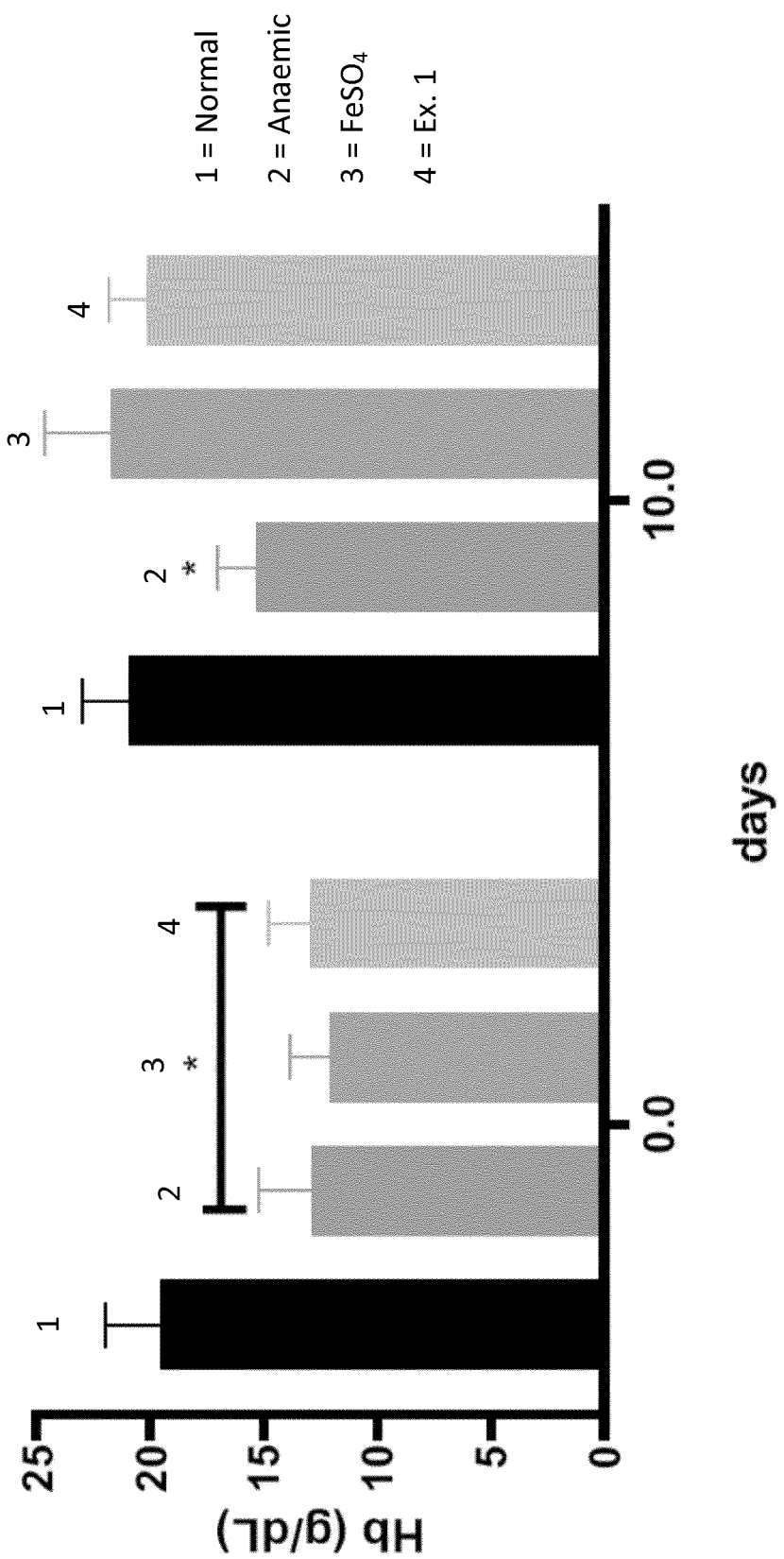
FIG. 9 is a bar chart showing the Hb (g/dL) in CD1 mice measured following the experiment as outlined in FIG. 8. n=6 mice, *p<0.05 in comparison with the control group using ANOVA one-way test.

The procedure for this study was adopted from well established techniques (Kajarabille et al, Brit. J. Nutrition, 117 (2017) 767-774) (FIG. 8). There was a change of haemoglobin levels between the anaemic (12.8±2.4 g/dL) and normal animals (19.55±2.4 g/dL) (FIG. 9). Both $FeSO_4$ and the formulation of Example 1 increased the haemoglobin levels in anaemic mice to those of normal mice. As shown in FIG. 9, at the start of the experiment (0 day) all groups had lower levels of haemoglobin in comparison with the control group. After 10 days of gavage with either $FeSO_4$ or Example 1 (Fe; 21 mM, 100 µl) both groups had recovered the Hb levels, and only the anaemic group had different values from the normal (control) group.

Hemoglobin Repletion Study

Male CD1 mice (3 weeks of age) were made Fe deficient by feeding a low-iron diet of 3-mg Fe/Kg diet based on the modified AIN-76A purified rodent diet (TD.80396; Harlan Teklad) for 3 weeks (i.e., until they were 6 weeks of age). Another group of mice were placed on a normal iron-sufficient diet (48-mg Fe/Kg diet) (TD.80394; Harlan Teklad) to serve as control. The diets were of identical composition except that the iron-sufficient diet contained iron added as ferric citrate. After this, blood was withdrawn from the tails to determine the initial Hb concentrations of the mice. The Fe-deficient mice were then divided into the treatment groups based on similar Hb concentrations. One group of the mice was maintained on the low-Fe diet with no iron supplementation (low-iron diet); the 2 other groups were gavaged daily with 150 mg Fe as $FeSO_4$ or as the dispersion of Example 1, for 10 days. After the 10 days, the mice were weighed, anaesthetized, and blood samples were taken for Hb, serum iron, and serum ferritin determinations. The mice were then killed by anaesthesia followed by neck dislocation, and the spleen, duodenum, kidney, and liver samples were excised, snap frozen in liquid nitrogen, and stored at −70° C. until further analysis.

Toxicity Studies

Anaemic CD1 mice were subjected to 10 days of oral gavage of the formulation of Example 1 (20 mM of Fe, 100 µL). After the last dose, the mice were provided with water ad libitum for 18 hours before sacrifice and collection of tissues. Tissues were stored at −70° C. until subjection to various toxicological investigations. There were 4 groups of animals; namely: non anaemic mice, anaemic mice, anaemic mice treated with $FeSO_4$, and anaemic mice treated with Example 1. Tests were made with respect to the following parameters:

1. Lipid peroxidation (MDA measurement)
2. GSH levels
3. Catalase levels
4. Non-heme iron levels
5. Plasma ferritin levels Methodology The collection of the duodenum was achieved by taking the first 5 cm after the pylorus. The section was opened transversally, and the mucosa was removed using a glass slide.

Lipid Peroxidation

Lipid peroxidation was measured by the detection of the endpoint product malondialdehyde (MDA), using the MDA microplate assay kit from Cohesion Biosciences (catalog number CAK1011). Liver tissue (70 mg) or duodenal mucosa (20 mg) were weighed and homogenized in assay buffer according with instructions of the kit manufacturer. All the samples were kept in ice during the assay. The dye reagent (Thiobarbituric acid) was brought at room temperature 30 min before the assay performance. The absorbance was measured at 532 and at 600 nm using a plate reader. The protein concentration of the extracts was analysed with the Bradford assay protocol and the MDA values were normalized against protein content.

GSH Levels

Reduced GSH was measured with an ELISA kit from MyBiosource company (Catalogue number MBS026635). The assay was performed according to manufacturer's instructions. Mice tissues were rinsed in PBS to take out the excess of blood, weighed (50 mg liver or 20 mg duodenal mucosa) and homogenized in PBS (pH 7.4) with a glass homogenizer on ice, and centrifuged at 3000 rpm for 20 min at 4° C. After centrifugation the samples were brought to room temperature and the supernatants were collected carefully. All reagents were at room temperature 20 min before use. A standard curve was made based on GSH antibody-GSH antigen interactions and Horseradish Peroxidase colorimetric detection system. Optical density (OD) was determined using a microplate reader at 450 nm within 10 min after adding the stop solution.

Catalase Levels

The activity of catalase enzyme was detected by using a Catalase Kit (Arbor assay company, Catalogue number K033-H1). Mice tissues were rinsed in PBS to take out the excess of blood and weighed (100 mg of liver or 20 mg duodenal mucosa). The procedure of sample preparation and assay was performed according to manufacturing instructions. The tissue samples were homogenized in ice-cold assay medium with a glass homogenizer, centrifuged at 10,000×g for 15 min at 4 degrees. The supernatant was collected to continue with the assay. A standard with catalase-hydrogen peroxide enzyme was measured within 30 min after reconstitution. The produced colour reaction was read at 450 nm using a plate reader.

Non-Heme Iron Levels

Non-heme iron was assayed according to the method of Foy et al. (Analytical Biochem. 1967; 18:559-563) as modified by Simpson & Peters (Br J Nutr. 1990; 63:79-89). Liver tissue was washed in ice-cold PBS, weighted (70 mg), and homogenized (1:5 w:v) in 0.15M NaCl-HEPES buffer (pH 7.4) with a glass Dounce homogenizer. 100 µl of the resulted extracted was boiled with 200 µl of TCA-sodium pyrophosphate and boil for 10 min, centrifuged at 10,000 RPM and collected the supernatant, the boiled extraction and centrifugation was repeated twice. From the total supernatant collection, 200 µL was mixed with 100 µL 4 of 0.23M ascorbic acid, 80 UL of 10 mM ferrozine and 420 µL of 2.0 M sodium-buffer acetate (pH 4.8). All samples were measured at 562 nm against the blank and compare with standard values.

Ferritin Levels

In this assay, the ferritin present in plasma samples reacts with the anti-Ferritin antibodies which have been adsorbed to the surface of polystyrene microliter wells. The assay was performed with a kit provided by Abcam company (Catalogue number, ab157713 Ferritin, mouse ELISA kit). The plasma samples were diluted 1:40 with the assay diluent provided in the kit. The amount of enzyme bound in the complex was measured by the addition of a chromo-genic substrate, 3,3',5,5'-tetramethylbenzidine (TMB). The colorimetric reaction was measured at 450 nm in a plate reader. The quantity of ferritin in the test sample was interpolated from the standard curve with known concentrations of ferritin.

Results

Figure 10:
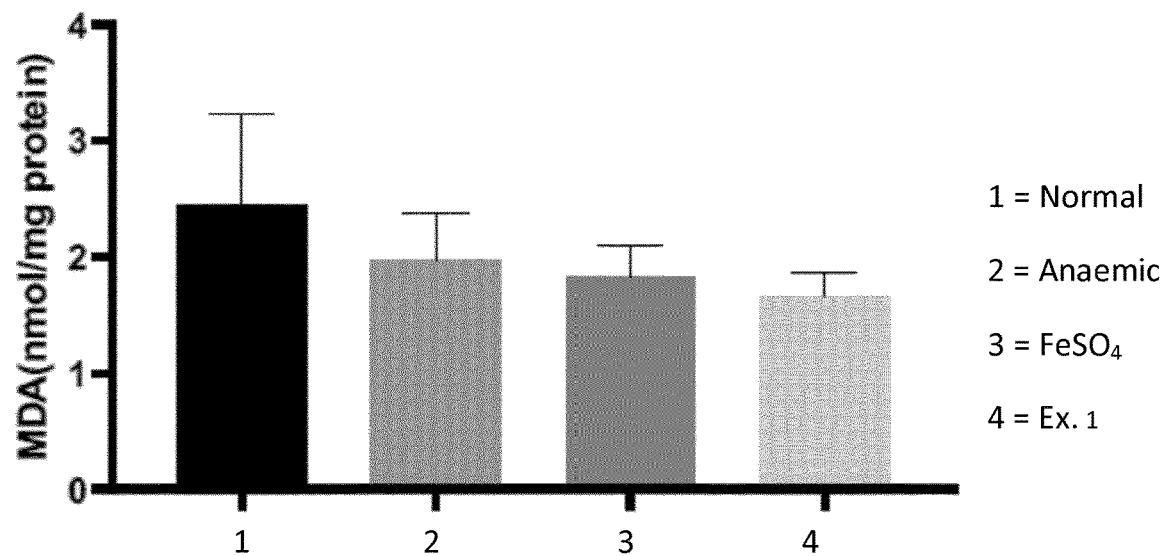
FIG. 10 is a bar chart showing the concentration of malondialdehyde (MDA), expressed in nmol/mg protein in liver of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days), n=6 mice per group. There were no statistical differences between the groups using ANOVA one-way test.
Figure 11:
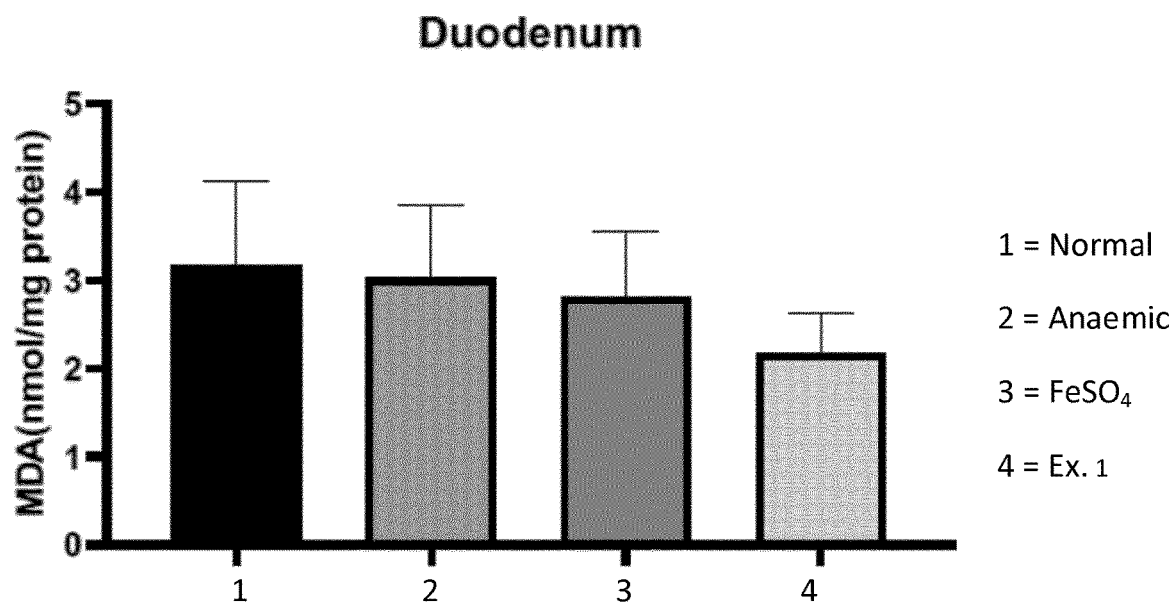
FIG. 11 is a bar chart showing the concentration of malondialdehyde (MDA), expressed in nmol/mg protein in duodenal mucosa of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days), n=6 mice per group. There were no statistical differences between the groups using ANOVA one-way test.

The MDA levels in the liver and duodenum are reported in FIGS. 10 and 11, respectively. There is a slight decrease in the MDA levels present in both tissues in the iron deficient mice, when compared with normal mice (N.S.). This is presumably associated with the lower levels of non-heme iron (labile iron pool). However, this difference is further increased (N.S.) in the mice treated with either $FeSO_4$ or Example 1. As seen in FIGS. 10 and 11, Example 1 is associated with the lowest levels of MDA. Clearly there is no increase in MDA in the presence of Example 1.

Figure 12:
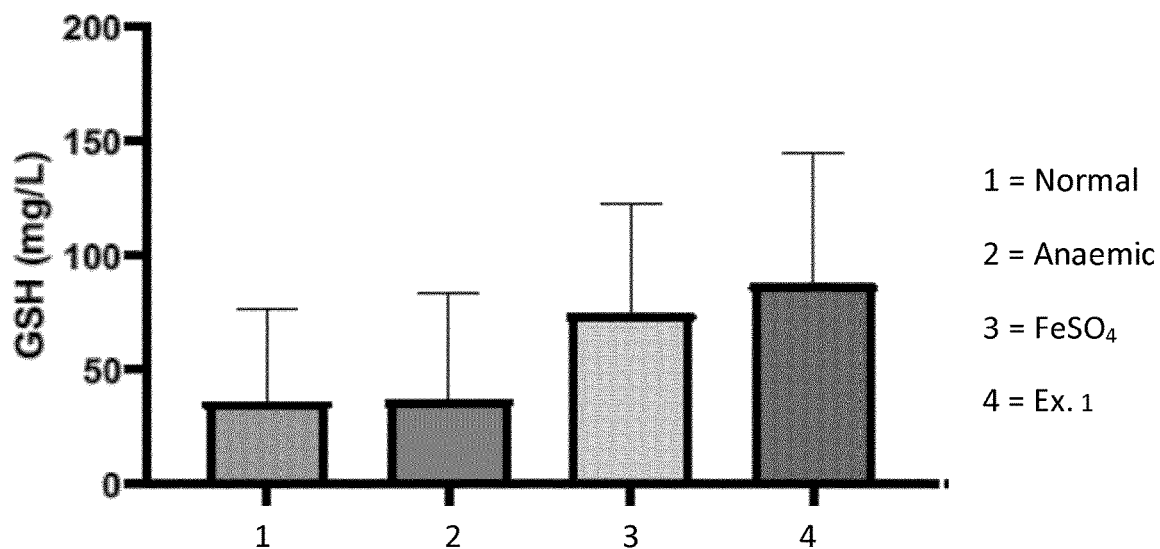
FIG. 12 is a bar chart showing the concentration of reduced GSH (mg/L) in liver of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days), measured by ELISA in 50 mg of liver wet tissue. n=6 mice per group. There were no statistical differences between the groups using ANOVA one-way test with liver tissue.
Figure 13:
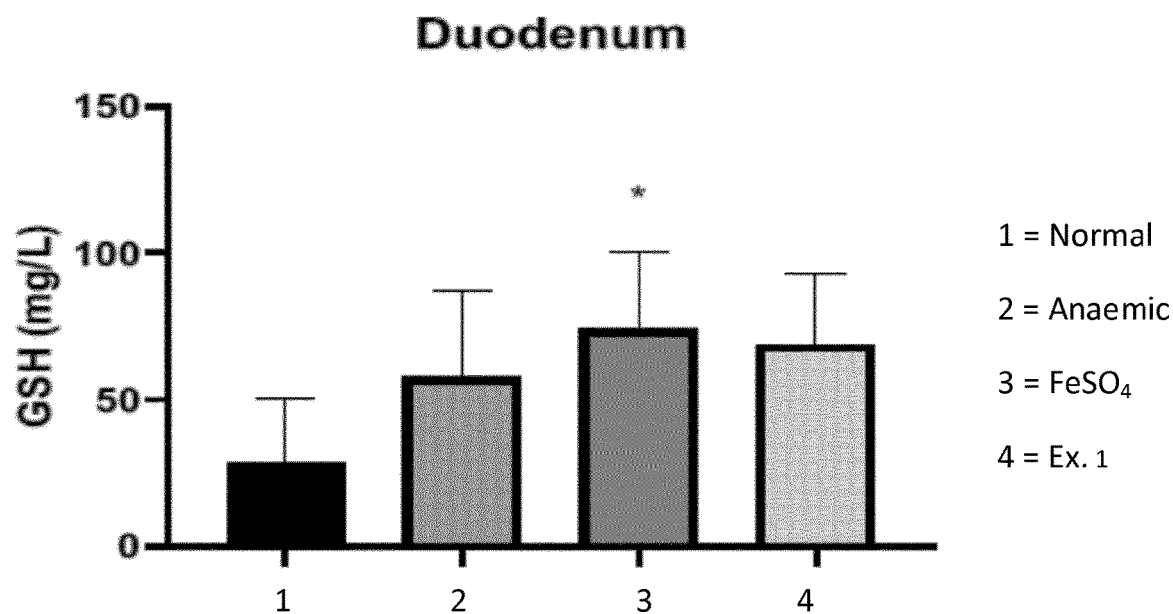
FIG. 13 is a bar chart showing the concentration of reduced GSH (mg/L) in duodenal mucosa of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days), measured by ELISA in 20 mg duodenal mucosa. n=6 mice per group. Only the $FeSO_4$-treated mice group presented higher levels of GSH in duodenum in comparison with the untreated group (P≤0.05, for ANOVA one-way test).

The level of reduced glutathione (GSH) in the different groups of animals is shown in FIGS. 12 and 13. There is a trend to increasing levels in the treated anaemic mice, indeed the difference was significant with $FeSO_4$ in the duodenum. This could be associated with the enhanced labile iron pool in the treated animals. GSH is not reduced in the presence of Example 1 and the levels are similar in animals treated with $FeSO_4$ and in those treated with Example 1.

Figure 14:
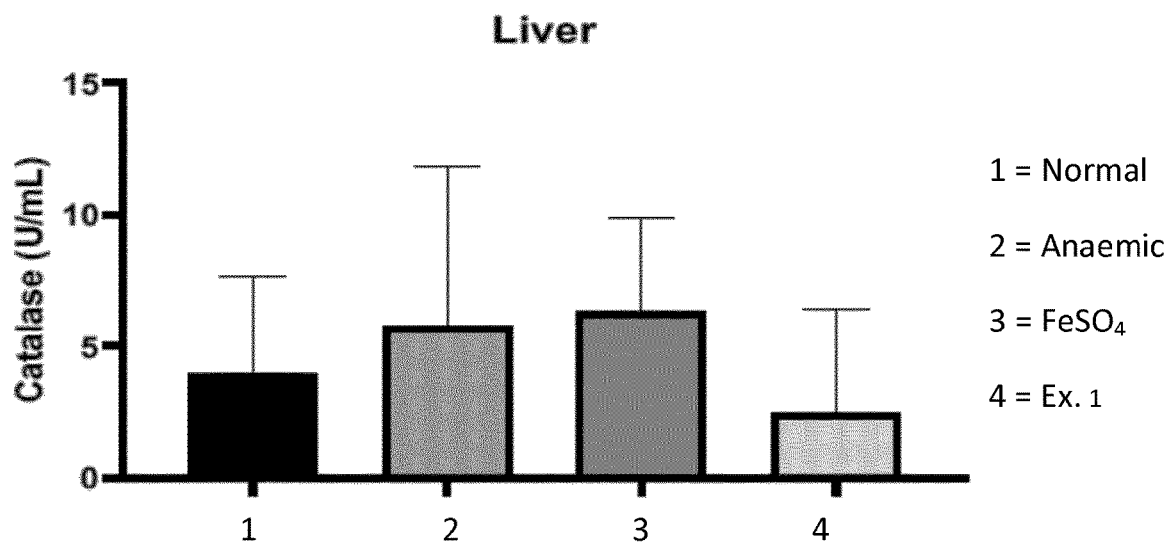
FIG. 14 is a bar chart showing the catalase activity in U/mL in liver of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days). n=6 mice per group. There were no statistical differences between the groups using ANOVA one-way test with liver tissue.
Figure 15:
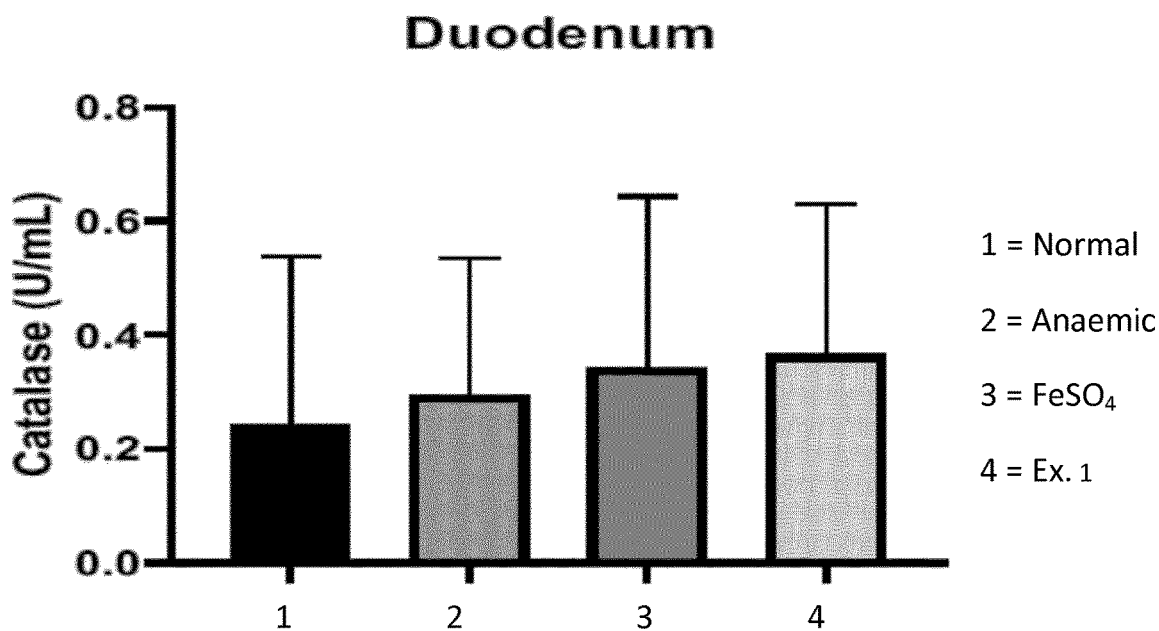
FIG. 15 is a bar chart showing the catalase activity in U/mL in duodenal mucosa of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days). n=6 mice per group. There were no statistical differences between the groups using ANOVA one-way test with liver tissue.

With catalase (FIGS. 14 and 15) no clear conclusions can be drawn from the study. The results were variable and so the average values were not significantly different from each other.

Figure 16:
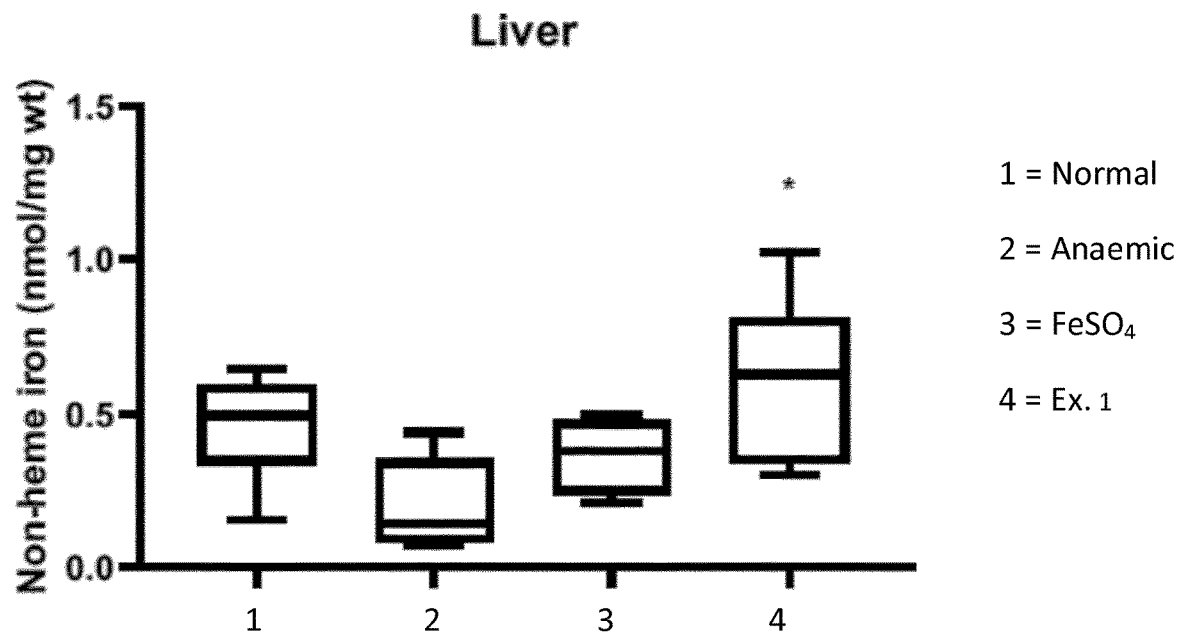
FIG. 16 is box a plot of the non-heme iron levels in liver of (1) normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days). The levels of non-heme iron in liver were significantly (p≤0.05, with ANOVA one-way test) higher in the group treated with Example 1, in comparison with the iron deficient group, and were similar to the control group. n=6 mice/group.

Non-heme iron levels in the liver of animals having received the inventive composition were substantially higher than the levels found in normal liver, anaemic liver and anaemic liver treated with $FeSO_4$. The measured values are shown in Table 6 and illustrated in FIG. 16.

TABLE 6

| Statistical values | Normal | Anaemic | Anaemic + $FeSO_4$ | Anaemic + Ex. 1 |
|---|---|---|---|---|
| Mean (nmol/mg) | 0.4603 | 0.1989 | 0.3637 | 0.6127 |
| Standard deviation (nmol/mg) | 0.1720 | 0.1483 | 0.1162 | 0.2680 |

Figure 17:
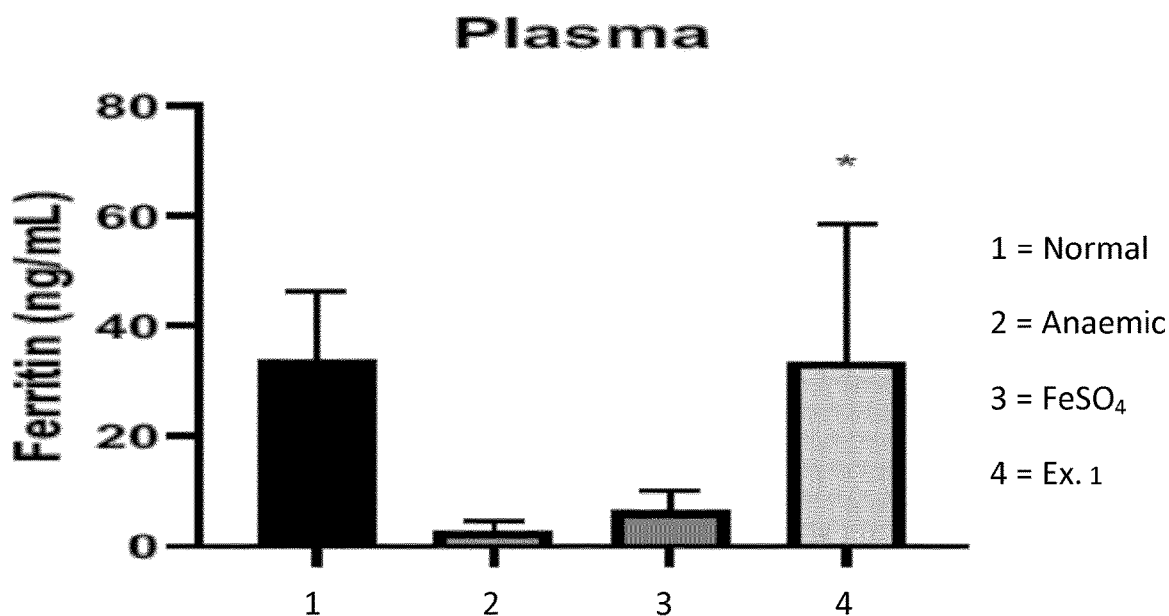
FIG. 17 is a bar chart representing the ferritin concentration in ng/ml in plasma of (1) mice normal mice, (2) anaemic mice, (3) anaemic mice treated with $FeSO_4$ (20 mM Fe, 100 µL, 10 days), and (4) anaemic mice treated with the formulation of Example 1 (20 mM Fe, 100 µL, 10 days). The levels of ferritin were higher in the group treated with the formulation of Example 1 than in the group treated with $FeSO_4$ (p≤0.05, with ANOVA one-way test). n=5 mice/group.

This is an excellent result and indicates that the composition of the invention is indeed effective at donating iron to the endogenous liver processes. This finding was confirmed by the plasma ferritin levels (FIG. 17) where Example 1 produced the highest level, similar to that of the untreated mice, whereas the plasma ferritin levels of iron deficient mice and of mice treated with $FeSO_4$ were both lower than that of normal mice. Plasma ferritin levels reflect the iron status of the liver.

Figure 18:
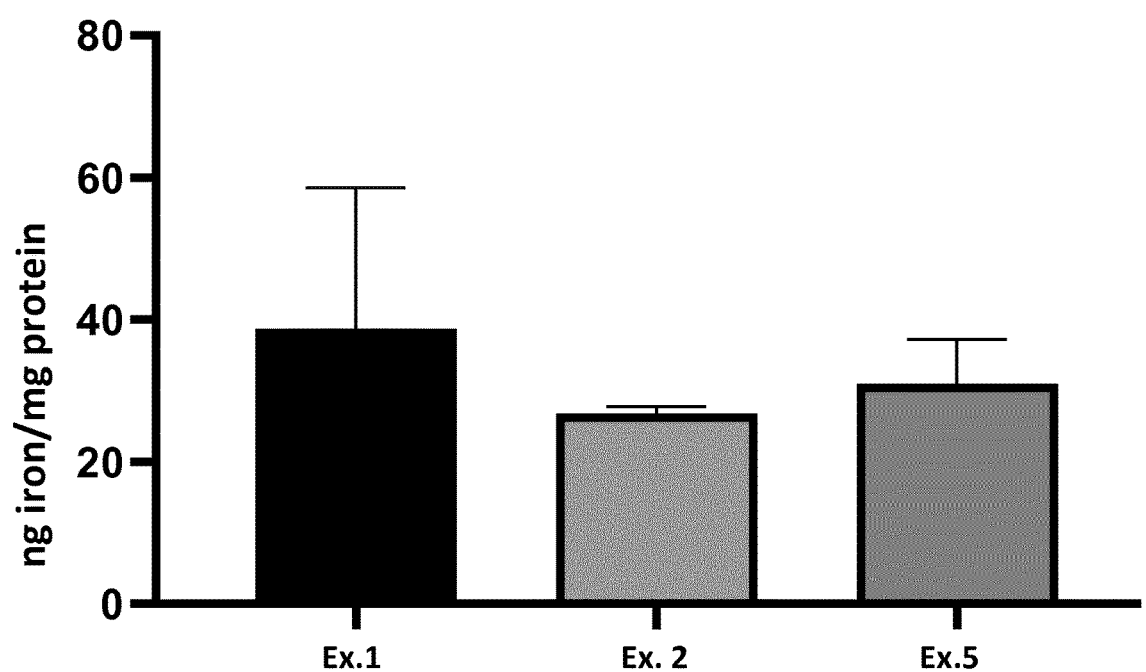
FIG. 18 is a bar chart showing the Caco-2 cell iron uptake, normalized by the total concentration of protein (ng Fe/mg protein), from three different inventive dispersions, prepared as described in Example 1, Example 2 and Example 5, respectively.

Uptake of Iron by Human Intestinal Caco-2 Cells from Different Compositions of the Invention The Caco-2 assay described herein above was repeated using as sources of iron, the dispersions of Example 1, Example 2 and Example 5, respectively, each containing iron at a concentration of 100 µM. The results are represented in FIG. 18.

The invention claimed is:

1. A composition comprising
   (i) an iron salt of a C12-C18 fatty acid;
   (ii) a citric acid ester of mono- and/or diglyceride or a mixture of citric acid esters of mono- and/or diglyceride; and
   (iii) a fatty acid or a salt thereof, or a mixture of fatty acids or fatty acid salts;
   wherein the composition comprises from 5 to 50% by weight of component (i), from 50 to 95% by weight of component (ii), and up to 20% by weight of component (iii);
   wherein the citric acid ester of mono- and/or diglyceride or mixture of citric acid esters of mono- and/or diglyceride comprises mono- and/or diglycerides of one or more C8-C24 fatty acids; and
   wherein component (iii) comprises one or more C8-C24 fatty acids or salts thereof.

2. The composition of claim 1, wherein the fatty acid is a saturated fatty acid.

3. The composition of claim 1, wherein the citric acid ester of mono- and/or diglyceride or mixture of citric acid esters of mono- and/or diglyceride comprises a monoesterified citric acid ester of mono- and/or diglyceride or mixture of monoesterified citric acid esters of mono- and/or diglyceride.

4. The composition of claim 1, wherein the weight ratio of component (ii) to component (i) is from 10:1 to 1:1.

5. A method for the treatment or prophylaxis of iron deficiency or a disorder associated with iron deficiency, the method comprising administering the composition of claim 1 to a mammal in need of such treatment.

6. The method of claim 5, wherein the treatment is by oral administration of said composition.

7. A pharmaceutical formulation comprising a therapeutically effective amount of a composition according to claim 1, and optionally a pharmaceutically acceptable excipient.

8. The pharmaceutical formulation of claim 7, wherein said composition constitutes from 1 to 99% by weight of the formulation.

9. The pharmaceutical formulation of claim 7, for oral administration.

10. The pharmaceutical formulation of claim 7, in the form of a hard capsule, a soft capsule, or a liquid.

11. A dietary supplement comprising the composition of claim 1.

12. A food additive comprising the composition according to claim 1.

13. A foodstuff comprising the composition according to claim 1.

14. A method for the preparation of an iron containing composition as set forth in claim 1, the method comprising:
   admixing components (i), (ii), and (iii);
   adding water and optionally a basifying agent; and
   processing the mixture to obtain a dispersion.

15. The composition of claim 1, wherein the weight ratio of component (ii) to component (i) is from 6:1 to 1:1.

* * * * *